United States Patent
Bucheli et al.

(10) Patent No.: US 6,790,650 B2
(45) Date of Patent: Sep. 14, 2004

(54) CACAO ENDOPROTEINASES AND PRODUCTION OF COCOA FLAVOR FROM SAME

(75) Inventors: Peter Bucheli, La Ville aux Dames (FR); Maryse Laloi, Tours (FR); James McCarthy, Noizay (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/339,351

(22) Filed: Jan. 10, 2003

(65) Prior Publication Data

US 2003/0148417 A1 Aug. 7, 2003

Related U.S. Application Data

(63) Continuation of application No. PCT/EP01/07255, filed on Jun. 26, 2001.

(30) Foreign Application Priority Data

Jul. 11, 2000 (EP) ............................................. 00114861

(51) Int. Cl.⁷ ............................ C12N 9/50; C12N 1/20; C12N 15/00; C07H 21/04
(52) U.S. Cl. ................ 435/219; 435/252.3; 435/320.1; 536/23.2
(58) Field of Search ............................. 435/219, 252.3, 435/320.1; 536/23.2

(56) References Cited

PUBLICATIONS

Accession No. T09739—sequence alignment with Applicants' SEQ ID No.: 1 & 2.*
Accession No. O04057—sequence alignment with Applicants' SEQ ID No.: 3.*

J. Voight et al., XP000972681, "Developmental stage–dependent variation of globular storage protein and aspartic endoprotease during ripening and germination of *Theobroma cacao* L. seeds," Journal of Plant Physiology, vol. 145, No. 3, pp. 299–307 (1995).

Hiraiwa Nagako et al. XP–000971170 "An aspartic endopepetidase is involved in the breakdown of propeptides of storage proteins in protein–storage vacuoles of plants," European Journal of Biochemistry, vol. 246, No. 1, 1997, pp. 133–141 (1997).

D'Arcy–Lameta et al. XP002155324 Molecular cloning and nucleotide sequence of cDNA encoding an aspartic proteinase from *Vigna unguiculata* leaves, Accession No. U61396 (1996).

J. Voight et al., XP002194847,"Precursors of the coca–specific aroma components are derived from the vicilin–class (7S) globulin of the cocoa seeds by proteolytic processing," Botanica Acta., vol. 148, No. 4, pp. 283–289, (1995), (abstract only).

* cited by examiner

*Primary Examiner*—Tekchand Saidha
(74) *Attorney, Agent, or Firm*—Winston & Strawn LLP

(57) ABSTRACT

The present invention pertains to novel aspartic endoproteinases from *Th. cacao* which are involved in the production of cocoa flavor and DNA sequences coding for them. These enzymes are advantageously used in the manufacture of cocoa flavor.

15 Claims, 14 Drawing Sheets

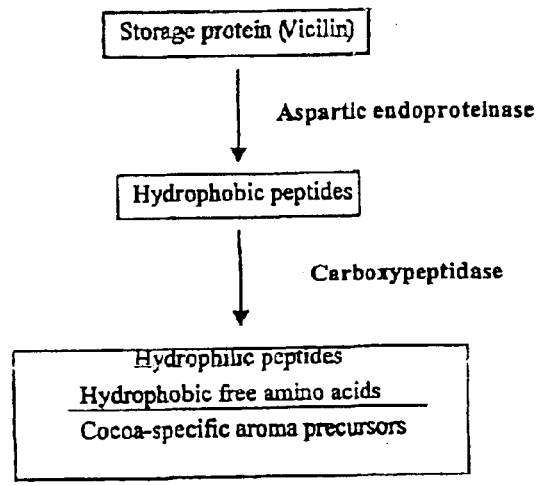
Fig. 1: Proteolytic formation of the cocoa-specific aroma
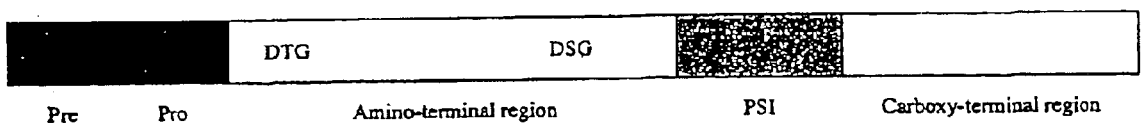
Fig. 2: Schematic representation of plant aspartic prepropeptides.

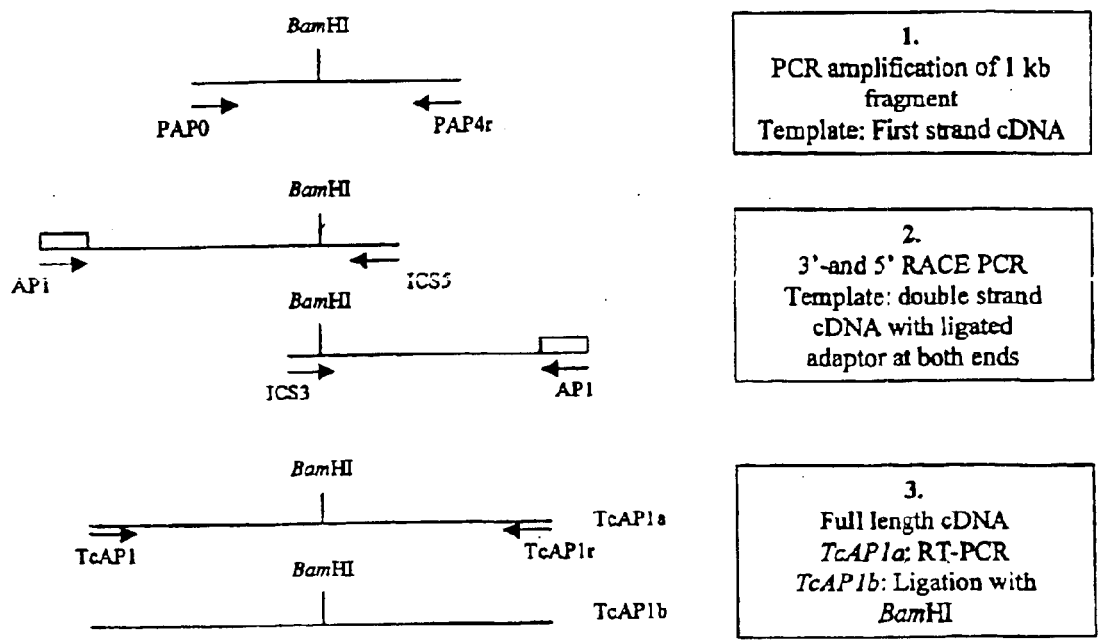
Fig. 3: Cloning strategy used for the isolation of cDNA encoding aspartic endoproteinase from *Theobroma cacao*,

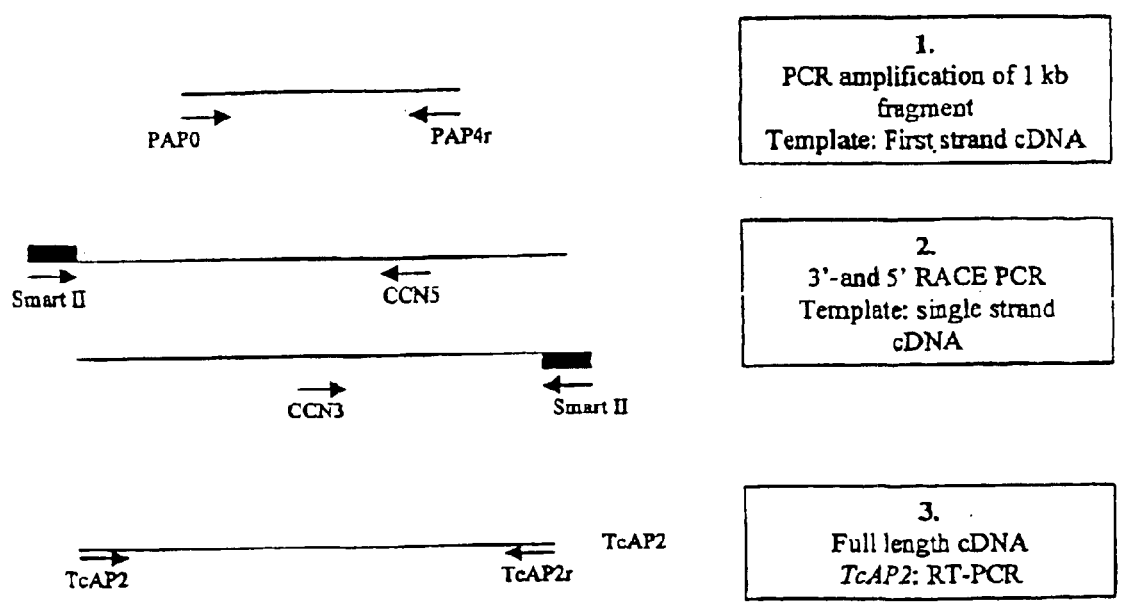
Fig. 4: Cloning strategy used for the isolation of cDNA encoding aspartic endoproteinase from *Theobroma cacao*,

```
                 10              20              30              40              50
TcAP1a  H G R I V K T T T V T L F L C L L L F P I V F S I S N E R L V R I G L K K R K F D Q N Y R L A A H L
TcAP1b  H G R I V K T T T V T L F L C L L L F P I V F S I S N E R L V R I G L K K R K F D Q N Y R L A A H L
TcAP2   H G T T I K V V V L S L F I S S L L F S V V S S V S M D G L V R I G L K K M K L D F H N R L A A R L 60              70              80              90             100
TcAP1a  D S K E R E A F R A S L K K Y R L Q G N L Q E S E D I D I V A L K N Y L D A Q Y F G E I G I G T P P
TcAP1b  D S K E R E A F R A S L K K Y R L Q G N L Q E S E D I D I V A L K N Y H D A Q Y F G E I G I G T P P
TcAP2   D S E D G E A L R A F I K K Y R F R N N L G D S E R T D I V A L K N Y H D A Q Y Y G E I G I G T P T 110             120             130             140             150
TcAP1a  Q N F T V I F D T G S S N L U V P S S K C Y F S I A C Y L H S R Y K S S R S S T Y K A H G K P A D I
TcAP1b  Q N F T V I F D T G S S N L U V P S S K C Y F S I A C Y L H S R Y K S S R S S T Y K A H G K P A D I
TcAP2   Q K F T V I F D T G S S N L U V S S T K C Y F S V A C Y F H S K Y E A S D S S T Y K D G K P A S I 160             170             180             190             200
TcAP1a  Q Y G T G A I S G F F S E D N V Q V G D L V V K M Q E F I E A T R E P S I T F L V A K F D G I L G L
TcAP1b  Q Y G T G A I S G F F S E D N V Q V G D L V V K N Q E F I E A T R E P S I T F L V T K F D G I L G L
TcAP2   Q Y G T G A I S G F F S Y D H V Q V G D L V V K D Q E F I E A T K E P G L T F M V A K F D G I L G L 210             220             230             240             250
TcAP1a  G F Q E I S V G N A V P V H Y N H V N Q G L V K E P V F S F H F N R D P E D D I G G E V V F G G H D
TcAP1b  G F Q E I S V G N A V P V H Y N H V N Q G L V K E P V F S F H F N R D P E D D I G G E V V F G G H D
TcAP2   G F K E I S V G D A V P V W Y N H I K Q G L T K E P V F S F N L H R N V D E E A G G E I V F G G V D 260             270             280             290             300
TcAP1a  P K H F K G D H T Y V P I T R K G Y H Q F D H G D V L I G N Q T T G L C A G G C S A I A D S G T S L
TcAP1b  P K H F K G D H T Y V P I T R K G Y H Q F D H G D V L I G N Q T T G L C A G G C S A I A D S G T S L
TcAP2   P N H Y K G K H T Y V P V T Q K G Y H Q F D H G D V L I A D K P T G Y C A G S C A A I A D S G T S L 310             320             330             340             350
TcAP1a  I T G P T A I I A Q V N H A I G A S G V V S Q E C K T V V S Q Y G E T I I D H L L S K D Q P L K I C
TcAP1b  I T G P T A I I A Q V N H A I G A S G V V S Q E C K T V V S Q Y G E T I I D H L L S K D Q P L K I C
TcAP2   L A G E S T V I T M I N H A I G A T G V V S Q E C K N V V Q Q T G R T I I D L L I A E A Q P Q K I C 360             370             380             390             400
TcAP1a  S Q I G L C T F D G T R G V S T G I E S V V H E H V G K A T G D L H D A H C S T C E H T V I H H Q N
TcAP1b  S Q I G L C T F D G T R G V S T G I E S V V H E N A G K A T G D L H D A H C S T C E H T V I H H Q N
TcAP2   S Q I G L C T F N G A H G V S T G I E S V V D E S N G K S S G V L R D A H C P A C E H A V V H H Q N 410             420             430             440             450
TcAP1a  Q L K Q H Q T Q E R I L E Y I N E L C D R L P S P H G E S A V D C S S L S T H P N V S F T I G G K I
TcAP1b  Q L K Q H Q T Q E R I L E Y I N E L C D R L P S P H G E S A V D C S S L S T H P N V S F T I G G K I
TcAP2   Q V R Q H Q T C D R I L S Y V N E L C D R V P N P H G E S A V D C G S L S S H P T I S F T I G G K V 460             470             480             490             500
TcAP1a  F E L S P E Q Y V L K V G E G D V A Q C L S G F T A L D V P P R G P L W I L G D V F H G Q F H T V
TcAP1b  F E L S P E Q Y V L K V G E G D V A Q C L S G F T A L D V P P R G P L W I L G D V F H G Q F H T V
TcAP2   F D L T P E E Y I L K V G E G S E A Q C I S G F T A L D I P P R G P L W I L G D I F M G R Y H T V

510
TcAP1a  F D Y G N L Q V G F A E A A
TcAP1b  F D Y G H L Q V G F A E A A
TcAP2   F D F G K L R V G F A E A A
```

FIG. 5

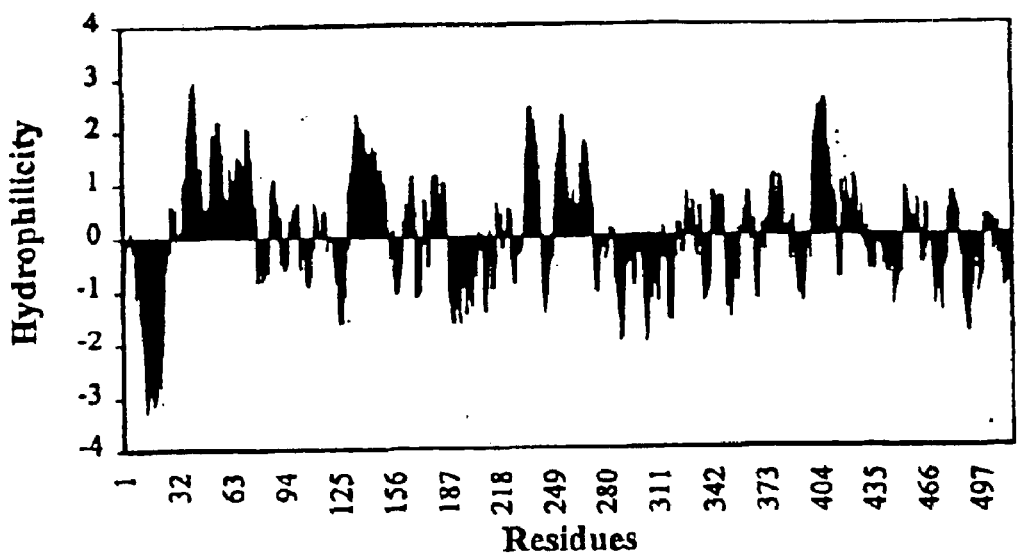
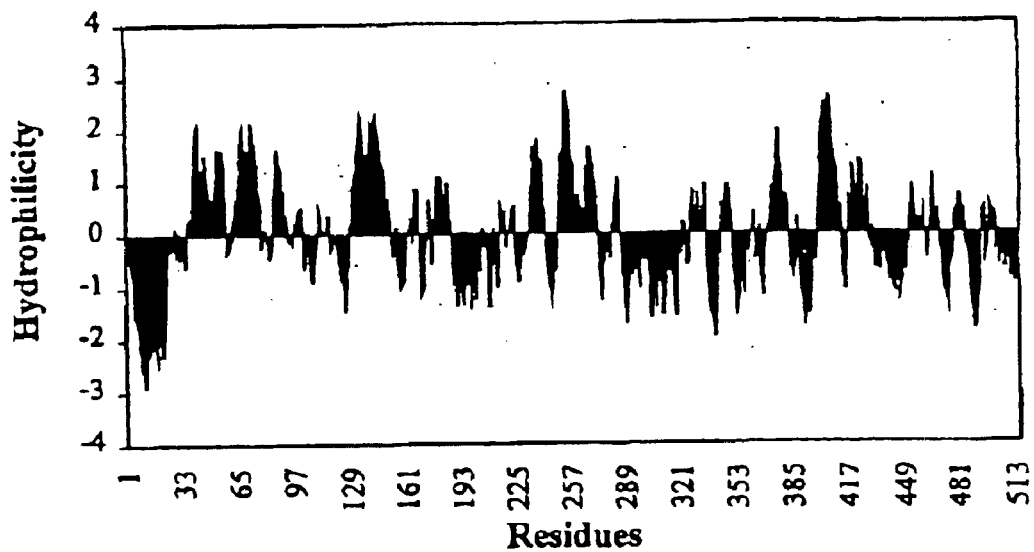
Fig. 6: Hydrophilicity Plot-Kyte-Doolittle for the TcAP1a (A) and TcAP2 (B) sequences.

SEQUENCE LISTING

<160> NUMBER OF SEQ ID NOS: 27

<210> SEQ ID NO 1
<211> LENGTH: 514
<212> TYPE: PRT
<213> ORGANISM: Theobroma cacao

<400> SEQUENCE: 1

```
Met Gly Arg Ile Val Lys Thr Thr Val Thr Leu Phe Leu Cys Leu
 1               5                  10                  15

Leu Leu Phe Pro Ile Val Phe Ser Ile Ser Asn Glu Arg Leu Val Arg
                20                  25                  30

Ile Gly Leu Lys Lys Arg Lys Phe Asp Gln Asn Tyr Arg Leu Ala Ala
            35                  40                  45

His Leu Asp Ser Lys Glu Arg Glu Ala Phe Arg Ala Ser Leu Lys Lys
         50                  55                  60

Tyr Arg Leu Gln Gly Asn Leu Gln Glu Ser Glu Asp Ile Asp Ile Val
 65                  70                  75                  80

Ala Leu Lys Asn Tyr Leu Asp Ala Gln Tyr Phe Gly Glu Ile Gly Ile
                85                  90                  95

Gly Thr Pro Pro Gln Asn Phe Thr Val Ile Phe Asp Thr Gly Ser Ser
                100                 105                 110

Asn Leu Trp Val Pro Ser Ser Lys Cys Tyr Phe Ser Ile Ala Cys Tyr
            115                 120                 125

Leu His Ser Arg Tyr Lys Ser Ser Arg Ser Ser Thr Tyr Lys Ala Asn
    130                 135                 140

Gly Lys Pro Ala Asp Ile Gln Tyr Gly Thr Gly Ala Ile Ser Gly Phe
145                 150                 155                 160

Phe Ser Glu Asp Asn Val Gln Val Gly Asp Leu Val Val Lys Asn Gln
                165                 170                 175

Glu Phe Ile Glu Ala Thr Arg Glu Pro Ser Ile Thr Phe Leu Val Ala
                180                 185                 190

Lys Phe Asp Gly Ile Leu Gly Leu Gly Phe Gln Glu Ile Ser Val Gly
            195                 200                 205

Asn Ala Val Pro Val Trp Tyr Asn Met Val Asn Gln Gly Leu Val Lys
    210                 215                 220

Glu Pro Val Phe Ser Phe Trp Phe Asn Arg Asp Pro Glu Asp Ile
225                 230                 235                 240

Gly Gly Glu Val Val Phe Gly Gly Met Asp Pro Lys His Phe Lys Gly
                245                 250                 255

Asp His Thr Tyr Val Pro Ile Thr Arg Lys Gly Tyr Trp Gln Phe Asp
                260                 265                 270

Met Gly Asp Val Leu Ile Gly Asn Gln Thr Thr Gly Leu Cys Ala Gly
            275                 280                 285
```

-continued

```
Gly Cys Ser Ala Ile Ala Asp Ser Gly Thr Ser Leu Ile Thr Gly Pro
        290                 295                 300

Thr Ala Ile Ile Ala Gln Val Asn His Ala Ile Gly Ala Ser Gly Val
305                 310                 315                 320

Val Ser Gln Glu Cys Lys Thr Val Val Ser Gln Tyr Gly Glu Thr Ile
                325                 330                 335

Ile Asp Met Leu Leu Ser Lys Asp Gln Pro Leu Lys Ile Cys Ser Gln
            340                 345                 350

Ile Gly Leu Cys Thr Phe Asp Gly Thr Arg Gly Val Ser Thr Gly Ile
        355                 360                 365

Glu Ser Val Val His Glu Asn Val Gly Lys Ala Thr Gly Asp Leu His
370                 375                 380

Asp Ala Met Cys Ser Thr Cys Glu Met Thr Val Ile Trp Met Gln Asn
385                 390                 395                 400

Gln Leu Lys Gln Asn Gln Thr Gln Glu Arg Ile Leu Glu Tyr Ile Asn
                405                 410                 415

Glu Leu Cys Asp Arg Leu Pro Ser Pro Met Gly Glu Ser Ala Val Asp
            420                 425                 430

Cys Ser Ser Leu Ser Thr Met Pro Asn Val Ser Phe Thr Ile Gly Gly
        435                 440                 445

Lys Ile Phe Glu Leu Ser Pro Glu Gln Tyr Val Leu Lys Val Gly Glu
    450                 455                 460

Gly Asp Val Ala Gln Cys Leu Ser Gly Phe Thr Ala Leu Asp Val Pro
465                 470                 475                 480

Pro Pro Arg Gly Pro Leu Trp Ile Leu Gly Asp Val Phe Met Gly Gln
                485                 490                 495

Phe His Thr Val Phe Asp Tyr Gly Asn Leu Gln Val Gly Phe Ala Glu
            500                 505                 510

Ala Ala
```

<210> SEQ ID NO 2
<211> LENGTH: 514
<212> TYPE: PRT
<213> ORGANISM: Theobroma cacao

<400> SEQUENCE: 2

```
Met Gly Thr Thr Ile Lys Val Val Leu Ser Leu Phe Ile Ser Ser
1               5                   10                  15

Leu Leu Phe Ser Val Val Ser Ser Val Ser Asn Asp Gly Leu Val Arg
            20                  25                  30

Ile Gly Leu Lys Lys Met Lys Leu Asp Pro Asn Asn Arg Leu Ala Ala
        35                  40                  45

Arg Leu Asp Ser Lys Asp Gly Glu Ala Leu Arg Ala Phe Ile Lys Lys
    50                  55                  60

Tyr Arg Phe Arg Asn Asn Leu Gly Asp Ser Glu Thr Asp Ile Val
65                  70                  75                  80

Ala Leu Lys Asn Tyr Met Asp Ala Gln Tyr Tyr Gly Glu Ile Gly Ile
                85                  90                  95

Gly Thr Pro Thr Gln Lys Phe Thr Val Ile Phe Asp Thr Gly Ser Ser
            100                 105                 110

Asn Leu Trp Val Ser Ser Thr Lys Cys Tyr Phe Ser Val Ala Cys Tyr
        115                 120                 125

Phe His Glu Lys Tyr Lys Ala Ser Asp Ser Ser Thr Tyr Lys Lys Asp
    130                 135                 140
```

```
Gly Lys Pro Ala Ser Ile Gln Tyr Gly Thr Gly Ala Ile Ser Gly Phe
145                 150                 155                 160

Phe Ser Tyr Asp His Val Gln Val Gly Asp Leu Val Val Lys Asp Gln
                165                 170                 175

Glu Phe Ile Glu Ala Thr Lys Glu Pro Gly Leu Thr Phe Met Val Ala
            180                 185                 190

Lys Phe Asp Gly Ile Leu Gly Leu Gly Phe Lys Glu Ile Ser Val Gly
        195                 200                 205

Asp Ala Val Pro Val Trp Tyr Asn Met Ile Lys Gln Gly Leu Ile Lys
    210                 215                 220

Glu Pro Val Phe Ser Phe Trp Leu Asn Arg Asn Val Asp Glu Ala
225                 230                 235                 240

Gly Gly Glu Ile Val Phe Gly Val Asp Pro Asn His Tyr Lys Gly
                245                 250                 255

Lys His Thr Tyr Val Pro Val Thr Gln Lys Gly Tyr Trp Gln Phe Asp
                260                 265                 270

Met Gly Asp Val Leu Ile Ala Asp Lys Pro Thr Gly Tyr Cys Ala Gly
            275                 280                 285

Ser Cys Ala Ala Ile Ala Asp Ser Gly Thr Ser Leu Leu Ala Gly Pro
        290                 295                 300

Ser Thr Val Ile Thr Met Ile Asn His Ala Ile Gly Ala Thr Gly Val
305                 310                 315                 320

Val Ser Gln Glu Cys Lys Ala Val Val Gln Gln Tyr Gly Arg Thr Ile
                325                 330                 335

Ile Asp Leu Leu Ile Ala Glu Ala Gln Pro Gln Lys Ile Cys Ser Gln
            340                 345                 350

Ile Gly Leu Cys Thr Phe Asn Gly Ala His Gly Val Ser Thr Gly Ile
        355                 360                 365

Glu Ser Val Val Asp Glu Ser Asn Gly Lys Ser Ser Gly Val Leu Arg
    370                 375                 380

Asp Ala Met Cys Pro Ala Cys Glu Met Ala Val Val Trp Met Gln Asn
385                 390                 395                 400

Gln Val Arg Gln Asn Gln Thr Gln Asp Arg Ile Leu Ser Tyr Val Asn
                405                 410                 415

Glu Leu Cys Asp Arg Val Pro Asn Pro Met Gly Glu Ser Ala Val Asp
            420                 425                 430

Cys Gly Ser Leu Ser Ser Met Pro Thr Ile Ser Phe Thr Ile Gly Gly
        435                 440                 445

Lys Val Phe Asp Leu Thr Pro Glu Glu Tyr Ile Leu Lys Val Gly Glu
    450                 455                 460

Gly Ser Glu Ala Gln Cys Ile Ser Gly Phe Thr Ala Leu Asp Ile Pro
465                 470                 475                 480

Pro Pro Arg Gly Pro Leu Trp Ile Leu Gly Asp Ile Phe Met Gly Arg
                485                 490                 495

Tyr His Thr Val Phe Asp Phe Gly Lys Leu Arg Val Gly Phe Ala Glu
                500                 505                 510

Ala Ala

<210> SEQ ID NO 3
<211> LENGTH: 514
<212> TYPE: PRT
<213> ORGANISM: Theobroma cacao

<400> SEQUENCE: 3
```

```
Met Gly Arg Ile Val Lys Thr Thr Thr Val Thr Leu Phe Leu Cys Leu
 1               5                  10                  15

Leu Leu Phe Pro Ile Val Phe Ser Ile Ser Asn Glu Arg Leu Val Arg
            20                  25                  30

Ile Gly Leu Lys Lys Arg Lys Phe Asp Gln Asn Tyr Arg Leu Ala Ala
        35                  40                  45

His Leu Asp Ser Lys Glu Arg Glu Ala Phe Arg Ala Ser Leu Lys Lys
    50                  55                  60

Tyr Arg Leu Gln Gly Asn Leu Gln Glu Ser Glu Asp Ile Asp Ile Val
65                  70                  75                  80

Ala Leu Lys Asn Tyr Met Asp Ala Gln Tyr Phe Gly Glu Ile Gly Ile
                85                  90                  95

Gly Thr Pro Pro Gln Asn Phe Thr Val Ile Phe Asp Thr Gly Ser Ser
            100                 105                 110

Asn Leu Trp Val Pro Ser Ser Lys Cys Tyr Phe Ser Ile Ala Cys Tyr
        115                 120                 125

Leu His Ser Arg Tyr Lys Ser Ser Arg Ser Ser Thr Tyr Lys Ala Asn
    130                 135                 140

Gly Lys Pro Ala Asp Ile Gln Tyr Gly Thr Gly Ala Ile Ser Gly Phe
145                 150                 155                 160

Phe Ser Glu Asp Asn Val Gln Val Gly Asp Leu Val Val Lys Asn Gln
                165                 170                 175

Glu Phe Ile Glu Ala Thr Arg Glu Pro Ser Ile Thr Phe Leu Val Thr
            180                 185                 190

Lys Phe Asp Gly Ile Leu Gly Leu Gly Phe Gln Glu Ile Ser Val Gly
        195                 200                 205

Asn Ala Val Pro Val Trp Tyr Asn Met Val Asn Gln Gly Leu Val Lys
    210                 215                 220

Glu Pro Val Phe Ser Phe Trp Phe Asn Arg Asp Pro Glu Asp Asp Ile
225                 230                 235                 240

Gly Gly Glu Val Val Phe Gly Gly Met Asp Pro Lys His Phe Lys Gly
                245                 250                 255

Asp His Thr Tyr Val Pro Ile Thr Arg Lys Gly Tyr Trp Gln Phe Asp
            260                 265                 270

Met Gly Asp Val Leu Ile Gly Asn Gln Thr Thr Gly Leu Cys Ala Gly
        275                 280                 285

Gly Cys Ser Ala Ile Ala Asp Ser Gly Thr Ser Leu Ile Thr Gly Pro
    290                 295                 300

Thr Ala Ile Ile Ala Gln Val Asn His Ala Ile Gly Ala Ser Gly Val
305                 310                 315                 320

Val Ser Gln Glu Cys Lys Thr Val Val Ser Gln Tyr Gly Glu Thr Ile
                325                 330                 335

Ile Asp Met Leu Leu Ser Lys Asp Gln Pro Leu Lys Ile Cys Ser Gln
            340                 345                 350

Ile Gly Leu Cys Thr Phe Asp Gly Thr Arg Gly Val Ser Thr Gly Ile
        355                 360                 365

Glu Ser Val Val His Glu Asn Ala Gly Lys Ala Thr Gly Asp Leu His
    370                 375                 380

Asp Ala Met Cys Ser Thr Cys Glu Met Thr Val Ile Trp Met Gln Asn
385                 390                 395                 400

Gln Leu Lys Gln Asn Gln Thr Gln Glu Arg Ile Leu Glu Tyr Ile Asn
                405                 410                 415
```

-continued

```
Glu Leu Cys Asp Arg Leu Pro Ser Pro Met Gly Glu Ser Ala Val Asp
            420                 425                 430
Cys Ser Ser Leu Ser Thr Met Pro Asn Val Ser Phe Thr Ile Gly Gly
        435                 440                 445
Lys Ile Phe Glu Leu Ser Pro Glu Gln Tyr Val Leu Lys Val Gly Glu
    450                 455                 460
Gly Asp Val Ala Gln Cys Leu Ser Gly Phe Thr Ala Leu Asp Val Pro
465                 470                 475                 480
Pro Pro Arg Gly Pro Leu Trp Ile Leu Gly Asp Val Phe Met Gly Gln
                485                 490                 495
Phe His Thr Val Phe Asp Tyr Gly Asn Leu Gln Val Gly Phe Ala Glu
            500                 505                 510
Ala Ala
```

<210> SEQ ID NO 4
<211> LENGTH: 1784
<212> TYPE: DNA
<213> ORGANISM: Theobroma cacao

<400> SEQUENCE: 4

```
tctgctcagc ttttcttgtc gaaatcatca ctaaaaccat ttgcggactt gcagttatca      60
gaatggggag aatagtcaaa actactacag tcactctttt tctttgtctt cttctgtttc     120
ctatcgtatt ttccatatcc aatgagagat tggtcagaat tggactgaaa agagaaagt     180
tcgatcaaaa ctatcggttg gctgcccacc ttgattccaa ggagagagag catttagag     240
cttctcttaa aaagtatcgt cttcaaggga acttacaaga gtctgaggac attgatattg     300
tggcactaaa gaactacttg gatgctcagt actttggtga gattggtatt ggcacacctc     360
cacagaactt cactgtgatt tttgacactg gtagttctaa tttgtgggtc ccttcatcta     420
agtgctattt ctcgatagct tgctatctcc attcaagata taaatcaagc cgttcaagca     480
cctacaaggc taatggtaaa ccagccgata tccaatacgg gactggagct atttctggat     540
tctttagtga ggacaatgta caagttggtg atcttgtagt taaaaatcag gaatttatcg     600
aggcaacaag ggagcccagc ataacatttt tggtggccaa gtttgatggg atacttggac     660
ttggatttca agagatttcg gttggaaatg ctgtgcctgt gtggtacaat atggtcaatc     720
aaggtcttgt taaggaacct gttttctcat tttggtttaa ccgcgatcct gaggatgata     780
taggtgggga agttgttttt ggtggaatgg atccaaaaca tttcaagggg gatcacactt     840
acgttcctat aacgcggaaa ggatactggc agtttgtgat gggtgatgtc ctgattggta     900
accaaacaac tggactttgt gctggtggct gcagtgcaat tgctgattct gggacttcct     960
tgataaccgg tcctacggct attattgctc aagtcaatca tgctattgga gcatcagggg    1020
ttgtaagtca agaatgcaag actgtagttt cacagtatgg agagacaata attgatatgc    1080
ttttatctaa ggaccaacca ctgaaaattt gctcacaaat aggtttgtgc acatttgatg    1140
gaactcgagg tgtaagtacg gggattgaaa gtgttgtgca tgagaatgtt gggaaagcca    1200
ctggtgattt gcatgatgca atgtgttcta cttgtgagat gacagttata tggatgcaaa    1260
accagcttaa gcagaaccag acacaggagc gtatacttga gtacatcaat gagctctgtg    1320
atcggttgcc tagtccaatg ggagaatcag ctgttgattg tagcagtcta tctaccatgc    1380
ctaatgtctc gttcacaatt ggtggaaaga tatttgagct cagccccgag cagtatgtcc    1440
tgaaagtggg tgagggagat gtagctcaat gcctcagtgg attcactgct ctggatgtgc    1500
cacctcctcg tggacctctc tggatcttgg gcgacgtctt tatgggccag ttccatacag    1560
```

-continued

```
tatttgacta tggcaacctg caagttggat ttgccgaggc tgcataagtg aaactttctg    1620
cttttataaa caacttcatg ttatgcagtg ctagtagtac ccttagaact gtggggatta    1680
agtatcaaat gataattgca tgtaaatatc tatgcaaaca tgatctgtga tcttcactgg    1740
atcgttgagt gtgatgcact tgtttaaga atttcatgtg atcc                     1784
```

<210> SEQ ID NO 5
<211> LENGTH: 1828
<212> TYPE: DNA
<213> ORGANISM: Theobroma cacao

<400> SEQUENCE: 5

```
gaccaacttt cctcttttct tgtttgact tcgccaaggt ggtttcgaca tttcggttaa      60
tatgggaacg actatcaaag tggttgtgct gtcgctgttc atctcgtccc tcttgttttc    120
tgtggtatct tctgtatcca atgatgggct ggttagaatc gggctgaaaa agatgaaact    180
ggatccaaat aaccggctcg ctgcccggct tgactccaag gacggagagg ccctcagagc    240
attcattaaa aagtatcgtt tccgtaataa tcttggagac tctgaggaga ctgatatcgt    300
tgcactaaag aactacatgg atgctcagta ctatggcgag attggtattg gaactccaac    360
acaaaagttc actgtgatat ttgacacagg aagctcaaat ctgtgggtat catcaaccaa    420
gtgctatttc tcggttgcat gttatttcca cgagaagtac aaggcaagcg attcaagtac    480
ctataagaag gatgggaaac ctgcttctat tcagtatggc actggagcta tttctggttt    540
ctttagttat gaccatgttc aagttggtga cttggttgtg aaagatcagg aatttattga    600
ggctactaag gagccaggtc ttacatttat ggtggccaaa tttgatggga tattaggact    660
tgggttcaag gagatttcag ttggggatgc tgtcccagtg tggtacaaca tgattaaaca    720
aggtcttatc aaggaaccag tatttcatt ttggcttaac cgcaatgtag atgaagaagc    780
aggtggtgaa attgttttg gcggggttga tccaaaccac tacaagggca agcacacata    840
tgttcctgta actcagaaag gctactggca gtttgacatg ggtgatgttc ttattgctga    900
caaaccaact ggatattgtg ctggcagctg tgccgcaatt gcagattctg gaacttcttt    960
gctggcaggt ccatcgactg tgattaccat gattaaccat gcaattggag ccactggagt    1020
ggttagccag gagtgcaagg cagtggttca acaatatggg cgaaccatca ttgatttact    1080
tatagctgag gcacaacctc agaagatctg ctcccaaatt ggattgtgca ctttaatgg    1140 tgctcatggt gttagcacgg gcattgagag tgtggtggat gagagcaatg gaaaatcatc    1200
tggagttctt cgtgatgcta tgtgccctgc ttgtgagatg gcagttgtgt ggatgcagaa    1260
ccaagtaagg cagaatcaga ctcaagaccg catattgagc tacgtaaatg agctttgtga    1320
tcgggtgcca aacccaatgg gagaatctgc tgttgactgc ggaagtcttt cttccatgcc    1380
tactatttcc ttcactattg gtggcaaagt ttttgacctc actccagaag agtatattct    1440
caaggtgggt gaaggttctg aagcacagtg catcagtggc tttactgctt tggatattcc    1500
tcctcctcgt ggacctctct ggattctggg agatatcttc atgggtcgct accacaccgt    1560 cttttgatttc ggtaaactga gagtcggctt cgccgaggcg gcataaaaga tctaccaggg    1620
ggaccccagt tttagttgt ccaccaacta ttatgttatc tgtaacttta taaagatgga    1680
ggaatcagcc taaaatcgtg ctgtgtgttg cttgtaaata ttccgccct tgctctgtt     1740 ctagaaacta ggatttgcct ttaggtcaaa gttgtcaaaa accaagtgag aaacgttgtg    1800
ctttgctttt tatcaacagt cacagata                                       1828
```

<210> SEQ ID NO 6
<211> LENGTH: 1784
<212> TYPE: DNA
<213> ORGANISM: Theobroma cacao

<400> SEQUENCE: 6

| | | | | | |
|---|---|---|---|---|---|
| tctgctcagc | ttttcttgtc | gaaatcatca | ctaaaaccat | ttgcggactt | gcagttatca | 60 |
| gaatggggag | aatagtcaaa | actactacag | tcactctttt | tctttgtctt | cttctgtttc | 120 |
| ctatcgtatt | ttccatatcc | aatgagagat | tggtcagaat | tggactgaaa | aagagaaagt | 180 |
| tcgatcaaaa | ctatcggttg | gctgcccacc | ttgattccaa | ggagagagag | gcatttagag | 240 |
| cttctcttaa | aaagtatcgt | cttcaaggga | acttacaaga | gtctgaggac | attgatattg | 300 |
| tggcactaaa | gaactacatg | gatgctcagt | actttggtga | gattggtatt | ggcacacctc | 360 |
| cacagaactt | cactgtgatt | tttgacactg | gtagttctaa | tttgtgggtc | ccttcatcta | 420 |
| agtgctattt | ttcgatagct | tgctatctcc | attcaagata | taaatcaagc | cgttcaagca | 480 |
| cctacaaggc | taatggtaaa | ccagccgata | tccaatacgg | gactggagct | atttctggat | 540 |
| tctttagtga | ggacaatgta | caagttggtg | atcttgtagt | taaaaatcag | gaatttatcg | 600 |
| aggcaacaag | ggagcccagc | ataacatttt | tggtgaccaa | gtttgatggg | atacttggac | 660 |
| ttggatttca | agagatttcg | gttggaaatg | ctgtgcctgt | gtggtacaat | atggtcaatc | 720 |
| aaggtcttgt | taaggaacct | gttttctcat | tttggtttaa | ccgtgatcct | gaggatgata | 780 |
| taggtgggga | agttgttttt | ggtggaatgg | atccaaaaca | tttcaagggg | gatcacactt | 840 |
| acgttcctat | aacgcggaaa | ggatactggc | agtttgatat | gggtgatgtc | ctgattggta | 900 |
| accaaacaac | tggactttgt | gctggtggct | gcagtgcaat | tgctgattct | gggacttcct | 960 |
| tgataaccgg | tcctacggct | attattgctc | aagtcaatca | tgctattgga | gcatcagggg | 1020 |
| ttgtaagtca | agaatgcaag | actgtagttt | cacagtatgg | agagacaata | attgatatgc | 1080 |
| ttttatctaa | ggaccaacca | ctgaaaattt | gctcacaaat | aggtttgtgc | acatttgatg | 1140 |
| gaactcgagg | tgtaagtacg | gggattgaaa | gtgttgtgca | tgagaatgct | gggaaagcca | 1200 |
| ctggtgattt | gcatgatgca | atgtgttcta | cttgtgagat | gacagttata | tggatgcaaa | 1260 |
| accagcttaa | gcagaaccag | acacaggagc | gtatacttga | gtacatcaat | gagctctgtg | 1320 |
| atcggttgcc | tagtccaatg | ggagaatcag | ctgttgattg | tagcagtcta | tctactatgc | 1380 |
| ctaatgtctc | gttcacaatt | ggtggaaaga | tatttgagct | cagccccgag | cagtatgtcc | 1440 |
| tgaaagtggg | tgagggagat | gtagctcaat | gcctcagtgg | attcactgct | ctggatgtgc | 1500 |
| cacctcctcg | tggacctctc | tggatcttgg | gcgacgtctt | tatgggccag | ttccatacag | 1560 |
| tatttgacta | tggcaacctg | caagttggat | ttgccgaggc | tgcataagtg | aaactttctg | 1620 |
| cttttataaa | caacttcatg | ttatgcagtg | ctagtagtac | ccttagaact | gtggggatta | 1680 |
| agtatcaaat | gataattgca | tgtaaatatc | tatgcaaaca | tgatctgtga | tcttcactgg | 1740 |
| atcgttgagt | gtgatgcact | tgtttaaga | atttcatgtg | atcc | 1784 |

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:artificial
<220> FEATURE:
<221> NAME/KEY: misc_feature
<222> LOCATION: (6)..(6)
<223> OTHER INFORMATION: any nucleotide

```
<220> FEATURE:
<221> NAME/KEY: misc_feature
<222> LOCATION: (9)..(9)
<223> OTHER INFORMATION: any nucleotide

<400> SEQUENCE: 7
gayacnggna gytcyaayyt vtgg                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:artificial
<220> FEATURE:
<221> NAME/KEY: misc_feature
<222> LOCATION: (8)..(8)
<223> OTHER INFORMATION: any nucleotide
<220> FEATURE:
<221> NAME/KEY: misc_feature
<222> LOCATION: (14)..(14)
<223> OTHER INFORMATION: any nucleotide

<400> SEQUENCE: 8
ccatmaanac rtcnccmarr atcc                                              24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:artificial

<400> SEQUENCE: 9
gcagccacca gcacaaagtc cag                                               23

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:artificial

<400> SEQUENCE: 10
cggttggaaa tgctgtgcct gtgtgg                                            26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:artificial

<400> SEQUENCE: 11
atgtgtgctt gcccttgtag tgg                                               23

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:artificial

<400> SEQUENCE: 12
ccgcaatgta gatgaagaag caggtgg                                           27

<210> SEQ ID NO 13
```

-continued

```
<211> LENGTH: 21
<212> TYPE: DNA
<213> ORGANISM: Artificial Sequence
<220> FEATURE:
<223> OTHER INFORMATION: Description of Artificial Sequence:artificial

<400> SEQUENCE: 13
tctgctcagc ttttcttgtc g                                              21

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:artificial

<400> SEQUENCE: 14
ggatcacatg aaattcttaa acaaagtgc                                      29

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:artificial

<400> SEQUENCE: 15
ctaatacgac tcactatagg                                                20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:artificial

<400> SEQUENCE: 16
atctgtgact gttgataaaa agc                                            23

<210> SEQ ID NO 17
<211> LENGTH: 8
<212> TYPE: PRT
<213> ORGANISM: Theobroma cacao

<400> SEQUENCE: 17

Asp Thr Gly Ser Ser Asn Leu Trp
  1               5

<210> SEQ ID NO 18
<211> LENGTH: 7
<212> TYPE: PRT
<213> ORGANISM: Theobroma cacao

<400> SEQUENCE: 18

Trp Ile Leu Gly Asp Val Phe
  1               5

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: artificial

<400> SEQUENCE: 19
ctatagggca agcagtggta acaac                                          25
```

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: artificial

<400> SEQUENCE: 20
tgacctaaag gcaaatccta gtttc                                    25

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: artificial

<400> SEQUENCE: 21
ccggcctctt cggccgccaa gcgaatatcc aatgagagat tggtcag            47

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: artificial

<400> SEQUENCE: 22
ccggcccacg tggccttagt ggtggtgtgc agcctcggca aatccaac           48

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: artificial

<400> SEQUENCE: 23
ccggcctctt cggccgccaa gcgagtatcc aatgatgggc tggttag            47

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: artificial

<400> SEQUENCE: 24
ccggcccacg tggccttagt ggtggtgtgc cgcctcggcg aagccgac           48

<210> SEQ ID NO 25
<211> LENGTH: 8
<212> TYPE: PRT
<213> ORGANISM: Theobroma cacao

<400> SEQUENCE: 25

Asp Ser Glu Glu Thr Asp Ile Val
 1               5

<210> SEQ ID NO 26
<211> LENGTH: 15
<212> TYPE: PRT
<213> ORGANISM: Theobroma cacao

<400> SEQUENCE: 26

```
Thr Val Ile Ser Thr Tyr Trp Gly Gln Asn Gly Phe Glu Gly Thr
 1               5                  10                  15

<210> SEQ ID NO 27
<211> LENGTH: 4
<212> TYPE: PRT
<213> ORGANISM: Theobroma cacao

<400> SEQUENCE: 27

Ala Asn Ser Pro
 1
```

CACAO ENDOPROTEINASES AND PRODUCTION OF COCOA FLAVOR FROM SAME

CROSS-REFERENCE TO RELATED APPLICATIONS

This application is a continuation of the US national phase designation of International application PCT/EP01/07255 filed Jun. 26, 2001, the content of which is expressly incorporated herein by reference thereto.

BACKGROUND ART

The present invention pertains to novel endoproteinases involved in the production of cocoa flavor and the DNA coding for them. In particular, the present invention relates to the use of said enzymes for the manufacture of cocoa flavor.

It is known that in processing cacao beans the generation of the typical cocoa flavor requires two steps—the fermentation step, which includes air-drying of the fermented material and the roasting step. Though roasting seems to be the key stage of obtaining cocoa flavor subjecting non fermented beans to a roasting step does not yield cocoa flavor suggesting that during the fermentation step precursors are produced that are essential for flavor generation (Rohan J. Food Sci. 29 (1964), 456–459).

During fermentation two major activities may be observed. First, the pulp surrounding the beans is degraded by micro-organisms with the sugars contained in the pulp being largely transformed to acids, especially acetic acid (Quesnel et al. J. Sci. Food. Agric. 16 (1965), 441–447; Ostovar and Keeney, J. Food. Sci. 39 (1973), 611–617). The acids then slowly diffuse into the beans and eventually cause an acidification of the cellular material. Second, fermentation also results in a release of peptides exhibiting differing sizes and a generation of a high level of hydrophobic free amino acids. This latter finding led to the hypothesis that proteolysis occurring during the fermentation step is not due to a random protein hydrolysis but seems to be rather based on the activity of specific endoproteinase (Kirchhoff et al., Food Chem 31 (1989), 295–311). This specific mixture of peptides and hydrophobic amino acids is deemed to represent cocoa-specific flavor precursors.

So far in cacao beans several proteolytic enzyme activities have been investigated and checked for their putative role in the formation of cocoa flavor precursors.

An aspartic endoproteinase activity which is optimal at very low pH (pH 3.5) and is inhibited by pepstatin A has been identified. A polypeptide described to have this activity has been isolated and is described to consist of two peptides (29 and 13 kDa) which are deemed to be derived by self-digestion from a 42 kDa pro-peptide (Voigt et al., J. Plant Physiol. 145 (1995), 299–307). The enzyme cleaves protein substrates between hydrophobic amino acid residues to produce oligopeptides with hydrophobic amino acid residues at the ends (Voigt et al., Food Chem. 49 (1994), 173–180). The enzyme accumulates with the vicilin-class (7S) globulin during bean ripening. Throughout germination, its activity remains constant during the first days and does not decrease before the onset of globulin degradation (Voigt et al., J. Plant Physiol. 145 (1995), 299–307).

A cysteine endoproteinase activity had been isolated which is optimal at a pH of 5. This enzymatic activity is believed not to split native storage proteins in ungerminated seeds. Cysteine endoproteinase activity increases during the germination process when degradation of globular storage protein occurs (Biehl et al., Cocoa Research Conference, Salvador, Bahia, Brasil, Nov. 17–23, 1996).

Moreover, a carboxypeptidase activity has been identified which is inhibited by PMSF and thus belongs to the class of serine proteases. It is stable over a broad pH range with a maximum activity at pH 5.8. This enzyme does not degrade native proteins but preferentially splits hydrophobic amino acids from the carboxy-terminus of peptides. Yet, peptides with carboxy-terminal arginine, lysine, or proline residues are seemingly resistant to degradation. The rate of hydrolysis has been found to be not only determined by the carboxy-terminal amino acid as such, but also to be affected by the neighbouring amino acid residue (Bytof et al., Food Chem. 54 (1995), 15–21).

During the second step of cocoa flavor production—the roasting step—the oligopeptides and amino acids generated at the stage of fermentation have been found to obviously undergo a Maillard reaction with reducing sugars present eventually producing the substances responsible for the cocoa flavor as such. This hypothesis has been confirmed in an experiment, wherein an oligopeptide fraction isolated after fermentation of cacao beans had been subjected to roasting in the presence of free amino acids and reducing sugars to obtain cocoa flavor (Mohr et al., Fette, Seifen, Anstrichmittel 73 (1971), 515–521 and 78 (1976), 88–95).

Cocoa-specific aroma has also been obtained in an experiment wherein acetone dry powder (AcDP) prepared from unfermented ripe cacao beans was subjected to autolysis at a pH of 5.2 followed by roasting in the presence of reducing sugars. It was conceived that under these conditions preferentially free hydrophobic amino acids and hydrophilic peptides should be generated and the peptide pattern thus obtained was similar to that of extracts from fermented cacao beans. An analysis of free amino acids revealed that Leu, Ala, Phe and Val were the predominant amino acids liberated in fermented beans or autolysis (Voigt et al., Food Chem. 49 (1994), 173–180). In contrast to these findings no cocoa-specific flavor could be detected when AcDP was subjected to autolysis at a pH of as low as 3.5, the pH, at which the known aspartic endoproteinase shows activity. Only few free amino acids were found to be released but a large number of hydrophobic peptides were formed. This may be explained by the aspartic endoproteinase having a high activity at this pH with the carboxypeptidase being substantially inactive under these conditions. When incubating peptides obtained after autolysis of AcDP at a pH of 3.5 with carboxypeptidase A from porcine pancreas at pH 7.5 hydrophobic amino acids were preferentially released. The pattern of free amino acids and peptides was rather similar to that found in fermented cacao beans and in the proteolysis product obtained by autolysis of AcDP at pH 5.2. After roasting of the amino acids and peptides mixture as above, a cocoa aroma could be generated. On the contrary, with a synthetic mixture of free amino acids alone whose composition was similar to the spectrum found in fermented beans cocoa flavor could not be detected after roasting, indicating that both the peptides and the amino acids are important for this purpose (Voigt et al., Food Chem. 49 (1994), 173–180).

Apart from the enzymes also the protein source of the peptides/amino acids seems to be of importance for the generation of cocoa flavor.

During cacao bean fermentation, the percentage reduction of protein concentration observed for vicilin and albumin was 88.8% and 47.4%, respectively (Amin et al., J. Sci. Food Agric. 76 (1998), 123–128). When peptides obtained by proteolysis of the globulin fraction were post-treated with carboxypeptidase, hydrophobic amino acids (Leu, Phe, Ala, Val, Tyr) were preferentially released and a typical cocoa aroma was detected after roasting in the presence of reducing sugars (Voigt et al., Food Chem. 50 (1994), 177–184). In contrary to that, the predominant amino acids released from the albumin-derived peptides were aspartic acid, glutamic acid and asparagine. Furthermore, no cocoa aroma was detected with the albumin fraction. It was therefore concluded that cocoa-specific aroma precursors are preferentially derived from the vicilin-like globulin of cacao bean. Consequently, the mixture of hydrophobic free amino acids and remaining oligopeptides required for the generation of the typical cocoa flavor components seems to be determined by the particular chemical structure of the cacao vicilin-class globulins.

These globulins isolated from cacao beans were also found to be efficiently degraded by pepsin (an aspartic endoproteinase) and chymotrypsin (a serine endoproteinase). Products derived from cacao globulins by successive proteolytic digestion with pepsin and carboxypeptidase A revealed a typical, but less pronounced cocoa aroma upon roasting. No cocoa aroma precursors were generated by degradation of globulins with chymotrypsin and carboxypeptidase A (Voigt et al., Food Chem, 51 (1994), 7–14). Therefore, the specific mixture of oligopeptides and hydrophobic free amino acids required for the formation of the typical cocoa aroma is not only determined by the structure of the protein substrate but also dependent on the specificity of the cacao enzyme cleaving the protein.

In view of the above data a hypothetical model for the generation of the said mixture of peptides and amino acids, i.e. the cocoa flavor precursors, during fermentation had been devised (FIG. 1), wherein in a first step peptides having a hydrophobic amino acid at their end, are formed from storage proteins, which peptides are subsequently further degraded. For splitting off hydrophobic amino acids from peptides formed in a preceding step the above carboxypeptidase activity seems to be involved. Yet, for the stage of producing the said peptides having C-terminal hydrophobic amino acids, the only known enzymatic activity which might be considered in this respect is an aspartic endoproteinase activity related to that mentioned above. It is also possible that the activity mentioned above is the result of different enzyme activities which are still unknown.

Though some aspects of cocoa flavor production have been elucidated there is still a need in the art to fully understand the processes going on, so that the manufacture of cocoa flavor may eventually be optimized.

SUMMARY OF THE INVENTION

The present invention discloses ways to improve the formation of cocoa flavor during processing and manufacturing. This is achieved in a first embodiment by providing tow novel aspartic endoproteinases derived from *Th. cacao* as identified by SEQ ID No 1 and SEQ ID No 2 or variants thereof obtained by substituting, deleting or adding one or more amino acids, an example of which is the protein identified by SEQ ID No 3, such that the enzymatic activity thereof is essentially retained. The aspartic endoproteinases described here (termed TcAP1 and TcAP2 in the following) are capable of cleaving the vicilin-class globulins isolated from cacao beans so that a successive degradation of the peptides by means of carboxypeptidase will result in a mixture of peptides and amino acids that yields a cocoa flavor upon a reaction with reducing sugars, e.g., upon roasting.

According to another embodiment, the present invention provides DNA sequences coding for the respective endoproteinases. The DNA sequences may be derived according to the genetic code from the amino acid sequences as identified under SEQ ID Nos. 1 and 2 considering the wobble hypothesis, optionally taking account codon preferences of specific hosts, in which the DNA sequences shall be expressed. The skilled person may well devise appropriate DNA sequences based on the polypeptide sequences given and his own technical knowledge and understanding. According to a preferred embodiment the DNA sequences are as identified as SEQ ID No 4 (TcAP1) and SEQ ID No 5 (TcAP2), which DNA sequence may be varied by replacing, deleting or adding one or more nucleotides such, that the endoproteinases essentially retain their enzymatic activity.

The DNA sequences may be used for recombinantly preparing the aspartic endoproteinases of the present invention. To this end the DNA sequences are incorporated into a suitable expression vector, such as a plasmid or a viral vector, which comprise the common sequences, such as a promotor, a polylinker for alleviating the cloning of the DNA sequences therein, leader sequences, to direct the polypeptide produced out of the cell. The vectors will be selected based on the requirements of the system used, e.g. for an expression in *E. coli* the vectors pGEMEX, pUC-derivates, pGEX-2T, pET-derivates, pQE8 may be envisaged, which are widespread in use and are commercially available. As an example aspartic endoproteinases could be expressed into medium or on surface of lactic acid bacteria used in lactic products such as milk or yogurt.

For expressing the endoproteinases in e.g., yeast the vectors pNFF296, pY100, pPIC9K, pPICz and Ycpad1 may be utilized and for expression in animal cells the vectors pKCR, pEFBOS, cDM8 und pCEV4 as well as pSS-derivates (Kay R. et al., Science 236 (1987), 1299–1302) may be used. Moreover, for expressing the endoproteinases in plant cells, especially in cacao, the vector pAL76 or pBin19-derivates may be used and for insect cells e.g. the vector pAcSGNT-A.

The aspartic endoproteinases may be expressed in a prokaryotic or eukaryotic cell as mentioned above. It will be appreciated that the skilled person will be able to select, based on the need and his own technical skill, an appropriate expression system to achieve the desired goal. In case the endoproteinase shall simply be added to a protein mixture, such as isolated cacao vicilin-class globulins, the recombinant enzyme may be produced in a bacterial system such as *E. coli* or in yeast and applied on the protein material.

Yet, in view of the implication to increase the enzymatic activity in cacao itself a transgenic plant cell may be envisaged, wherein one or more copies of the endoproteinases, optionally coupled with a suitable and controllable promotor, have been incorporated into the genome of the plant cell. The introduction of the DNA sequence(s) may be achieved by e.g., homologous recombination of DNA stretches harboring one or more copies of the DNA sequences coding for the endoproteinases of the present invention into embryogenic calli prepared beforehand. Since plant cells are totipotent a new transgenic cacao tree may be produced in this way the beans of which will exhibit more rapid degradation of the vicilin-class globulins when subjected to conditions of fermentation.

In consequence a transgenic plant, harboring one or more additional copy(ies) of a DNA sequence coding for the endoproteinases of the present invention is well within the scope of the present invention.

The present endoproteinases may also be used for the manufacture of cocoa flavor by treating a suitable starting material (cacao bean, liquor or crumb), preferably vicilin-class globulins, with said endoproteinases of the present invention and concurrently or afterwards treating the material with carboxypeptidase to obtain a mixture of peptides and amino acids appropriate to act as cocoa flavor precursors. This mixture may then be subjected to "a roasting step", i.e. may be subjected to a reaction with reducing sugars to eventually obtain cocoa flavor.

Since some of the enzymes involved in the generation of cocoa flavor are now at hand cocoa flavor may be produced artificially without having to rely on the common process of fermenting and roasting cacao beans. The present invention therefore also provides a method for generating cocoa flavor which comprises the step of subjecting a material suitable to yield cocoa flavor precursors, such as the known vicilin-class globulins, to an enzymatic degradation involving the use of the aspartic endoproteinases of the present invention.

In particular, the present aspartic endoproteinases may be overexpressed in protein bodies of plant cells, especially seed cells, and then hydrolysis of the cellular protein material may be effected by treating such plant cells with an acidic solution.

The present endoproteinases may also be used for hydrolyzing proteins by contacting a material of choice, such as the protein in isolated form or material containing the protein, such as e.g. food material, with an endoproteinase of the present invention and effecting hydrolysis to a desired degree. Examples for materials are dairy substances (whey protein, and casein), wheat gluten, corn gluten, meat, egg protein and other protein containing vegetable substances not mentioned above such as proteins from oil seeds, including soybean protein and defatted soy protein.

BRIEF DESCRIPTION OF THE DRAWING FIGURES

In the figures,

FIG. 1 shows the theoretical production process of cocoa specific flavor precursors;

FIG. 2 shows a schematic representation of plant aspartic prepropeptides;

FIG. 3 schematically shows the cloning strategy for the isolation of the endoproteinase TcAP1 cDNA (SEQ ID No. 4);

FIG. 4 schematically shows the cloning strategy for the isolation of the endoproteinase TcAP2 cDNA (SEQ ID No. 5);

FIG. 5 shows a comparison between the different polypeptides obtained;

FIG. 6 shows a hydrophilicity Kyte Doolitle plot for both endoproteinases obtained.

Figure 7:
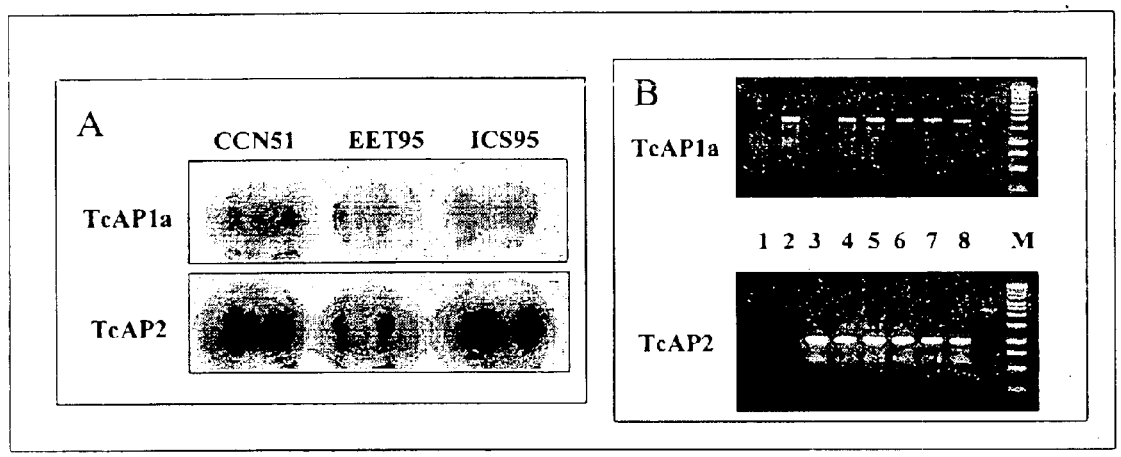
Figure 8:
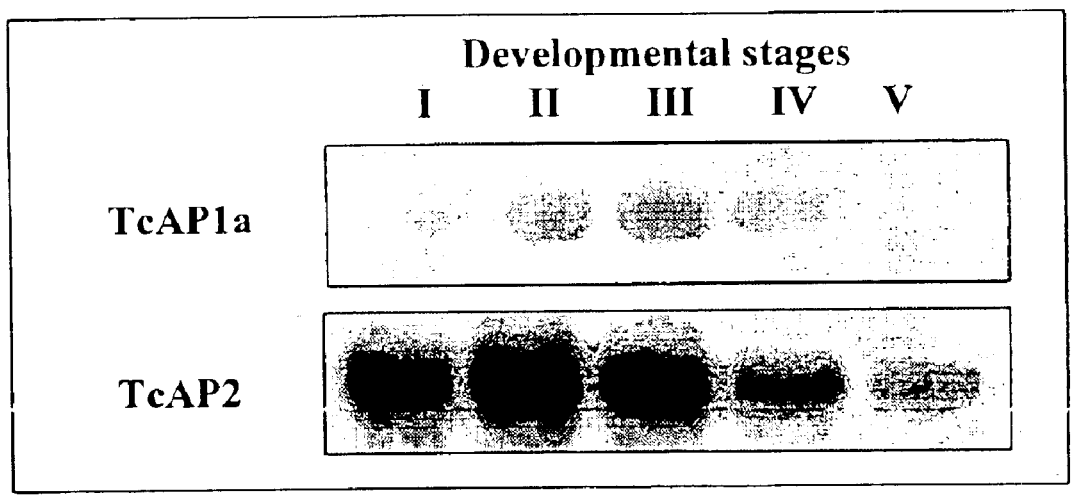
Figure 9:
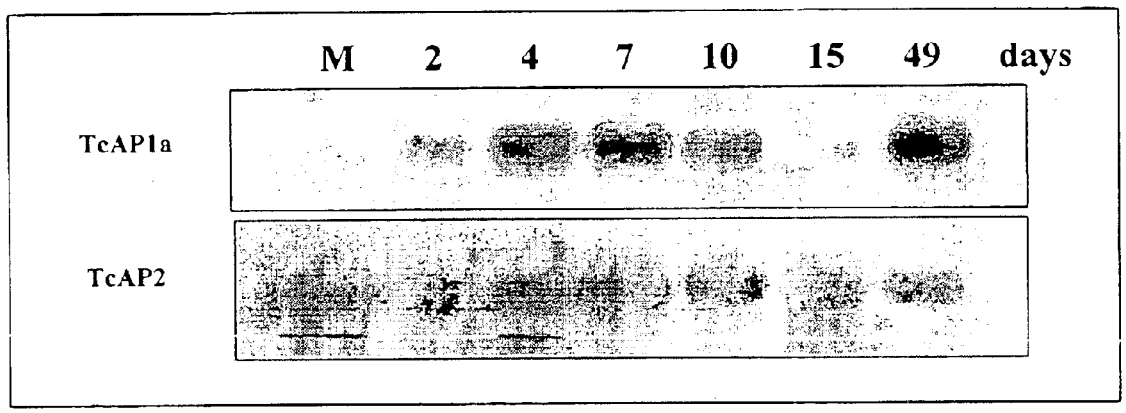
Figure 10:
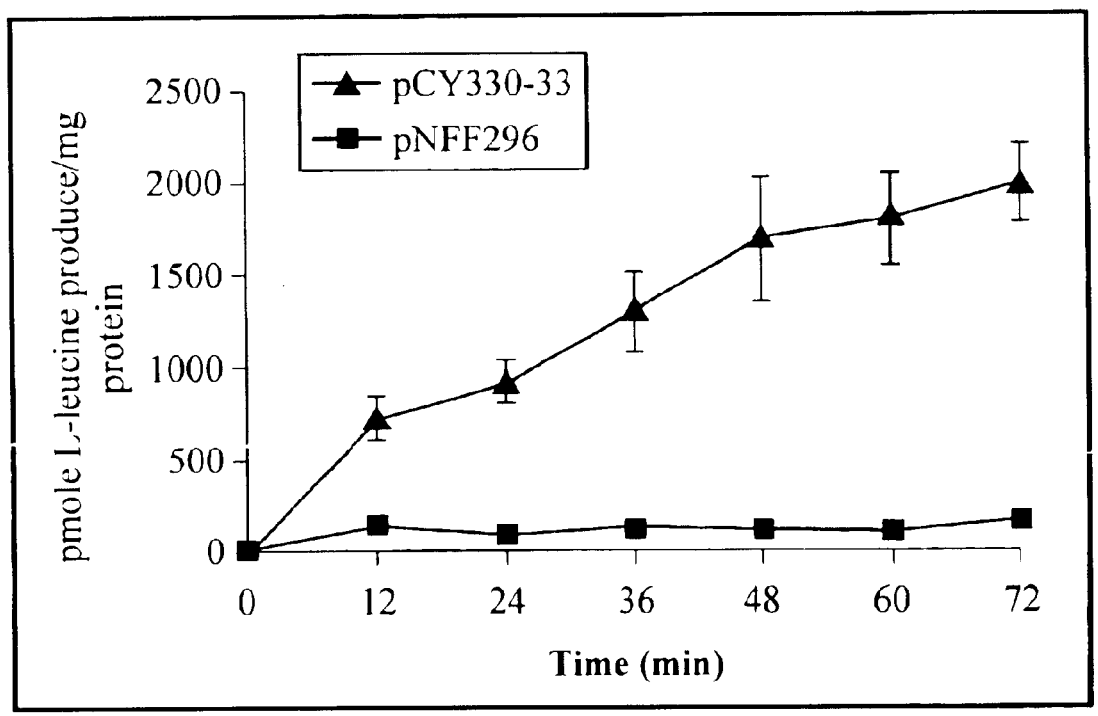
Figure 11:
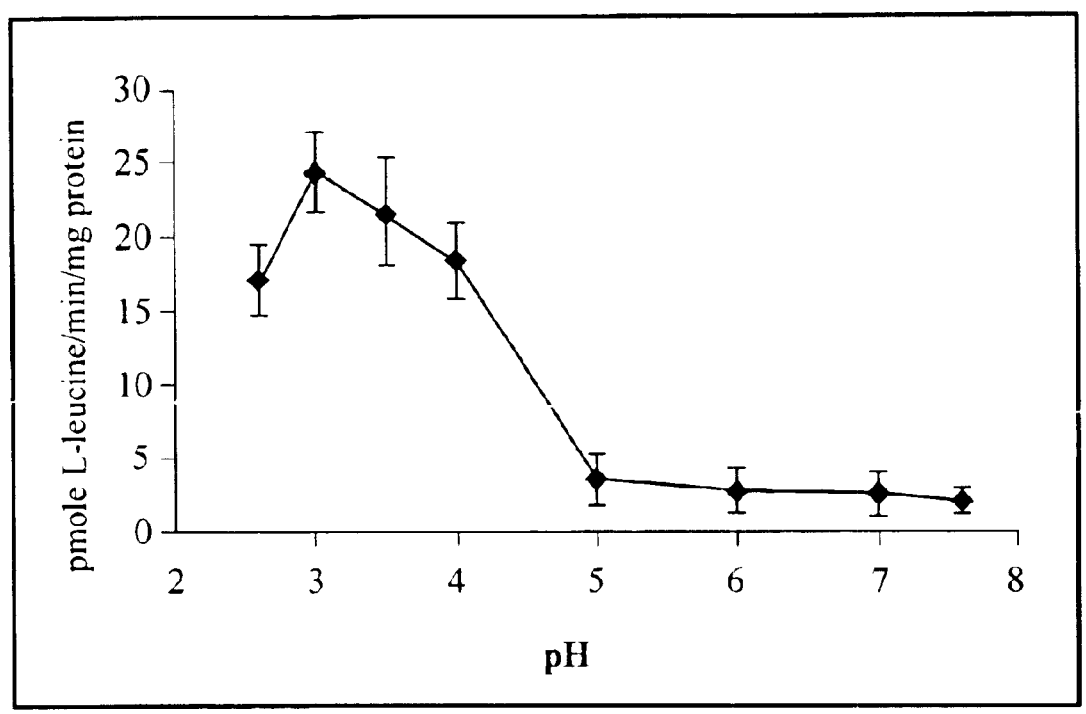
Figure 12:
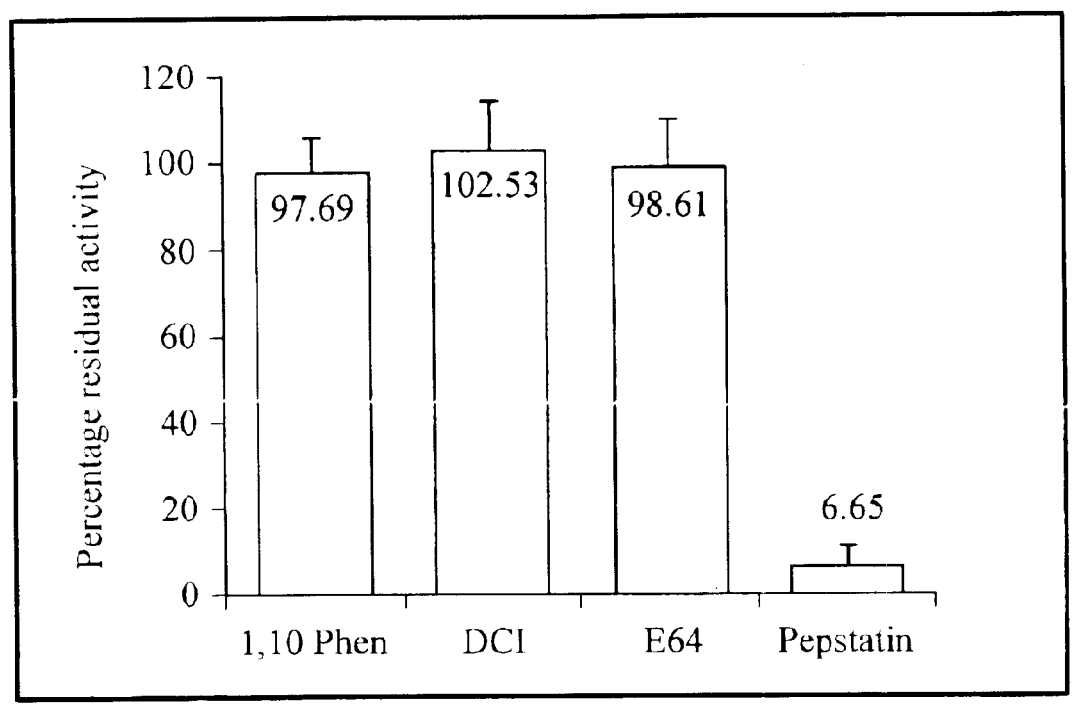
Figure 13:
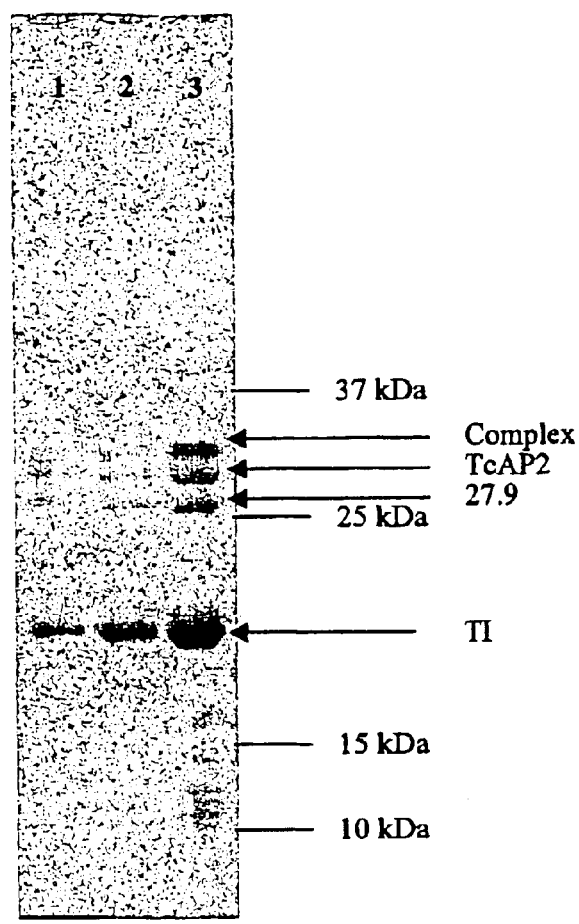
Figure 14:
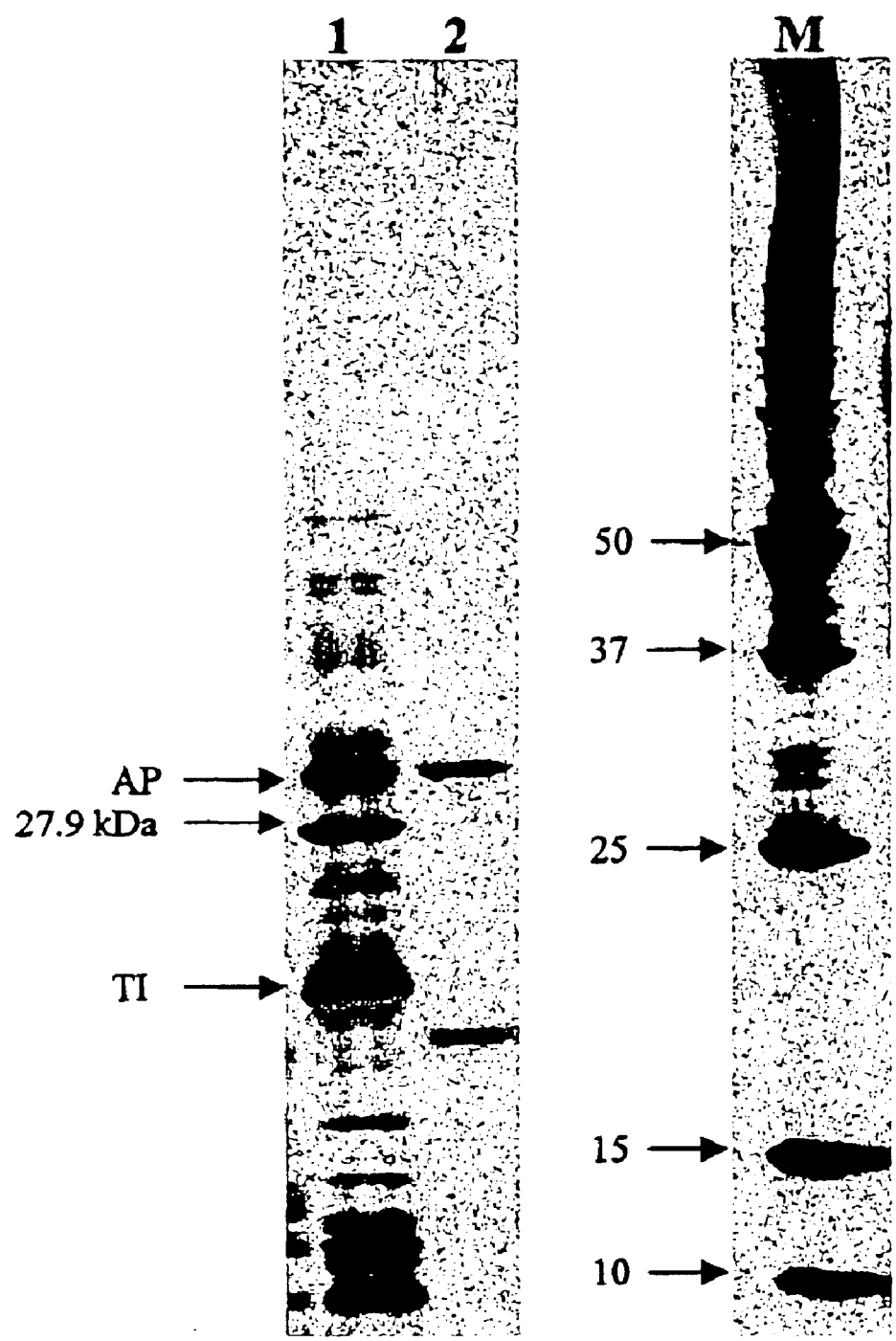
Figure 15:
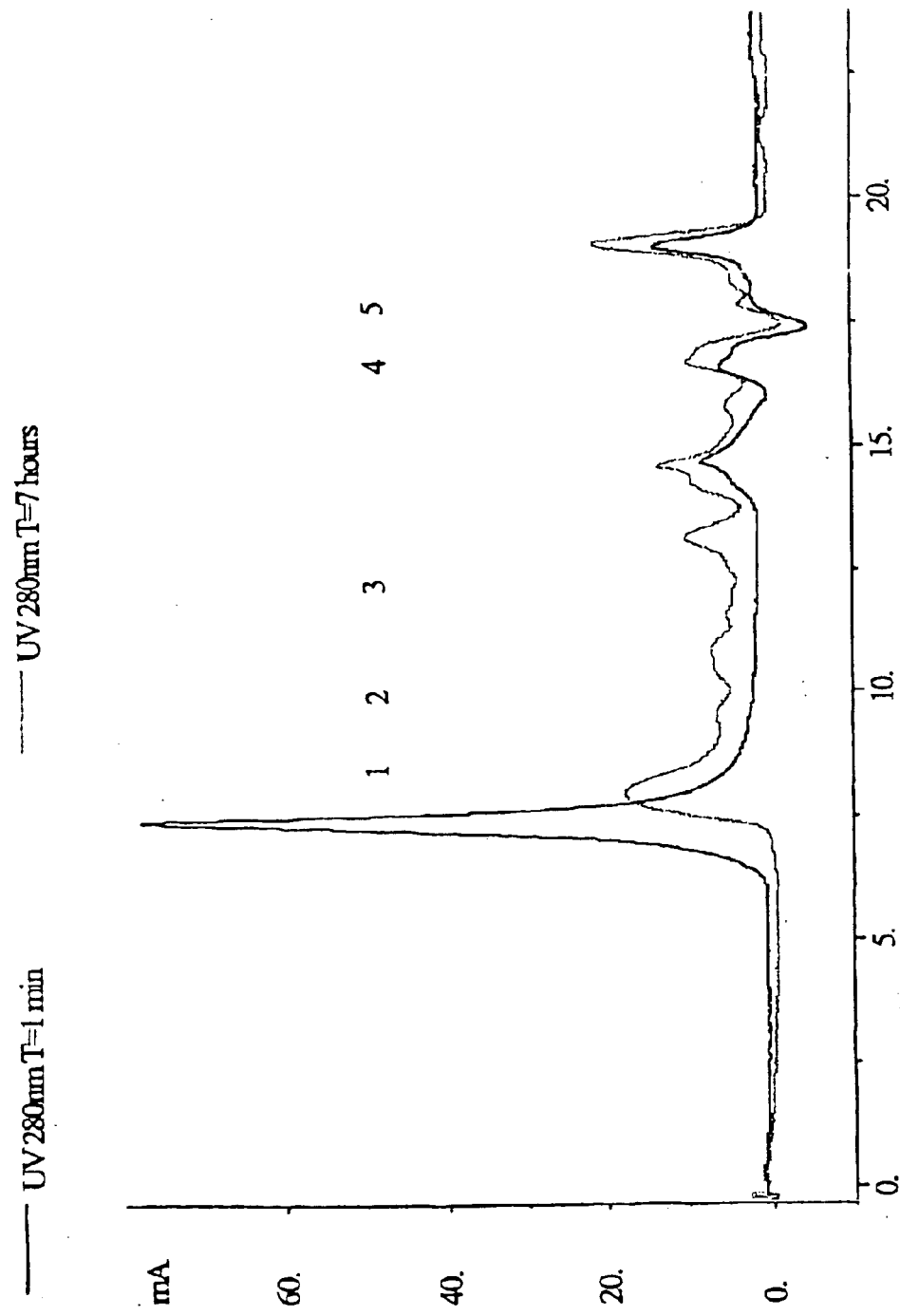

FIG. 7 shows the expression of TcAP1a (SEQ ID No. 1) and TcAP2 (SEQ ID No. 2) in cacao beans of three different cacao clones, CCN51, EET95, ICS95. A: Northern blot analysis of TcAP1a and TcAP2 expression. For each lane 15 $\mu$g total RNA were used. Membranes were probed either with radiolabelled TcAP1a probe and exposed for 8 days or with radiolabelled TcAP2 probe and exposed overnigth. B: RT-PCR performed with water (1), TcAP1a plasmid (2), TcAP2 plasmid (3), ICS95 leaf cDNA (4), ICS95 bean cDNA (5, 6), EET95 bean cDNA (7) and CCN51 bean cDNA (8) as template;

FIG. 8 shows the results of a Northern blot analysis of TcAP1a and TcAP2 expression in cacao beans from clone CCN51 at different maturation stages. I: white embryos from violet 360 g fruits. II: violet embryos from violet 360 g fruits. III: violet embryos from violet 790 g fruits. IV: violet embryos from violet 1150 g fruits. V: mature beans from red 1100 g fruits. For each lane 15 $\mu$g total RNA were used. Membranes were probed either with radiolabelled TcAP1a probe and exposed for 8 days or with radiolabelled TcAP2 probe and exposed for 3 days;

FIG. 9 shows the results of a Northern blot analysis of TcAP1a and TcAP2 expression in cacao bean produced by cacao clone CCN51 at different germination stages. Mature bean were germinated in vermiculite. For each lane 15 $\mu$g total RNA were used. Membranes were probed either with radiolabelled TcAP1a probe and exposed for 8 days or with radiolabelled TcAP2 probe and exposed overnight;

FIG. 10 shows the results of a Hydrolysis of bovine haemoglobin by recombinant TcAP2 protein in yeast culture medium and comparison with control strain pNFF296. Data are means of 3 measurements±SD;

FIG. 11 shows the results of experiments determining the pH dependence of haemoglobin hydrolysis by recombinant TcAP2. Enzyme assay was performed at indicated pH for 1 hour. Data are means of 9 measurements (three experiments) ±SD;

FIG. 12 shows the effect of different inhibitors on the hydrolysis of bovine haemoglobin by recombinant TcAP2. Inhibitors were added in the reaction at final concentration of 2 mM for 1.10 phenanthroline, 100 $\mu$M DCI, 10 $\mu$M E64 and 2 $\mu$M pepstatin. Activity at pH 3 without inhibitor was taken as 100% and correspond to 28.8±3.8 pmoles L-leucine produced/min/mg protein. Data are means of 3 measurements±SD;

FIG. 13 shows the analysis of most active pool (fractions 57–64) from the Sephacryl S-200 HiPrep 16/60 size exclusion column on a 10–20% Gradient SDS-PAGE Gel (Coomassie stained). In lanes 1–3, 12, 24, and 40.8 $\mu$g protein was loaded in each lane respectively. Complex denotes a putative covalent complex between AP and trypsin inhibitor fragments; TcAP2 denotes the 30.5 kDa polypeptide; 27.9 denotes the 27.9 kDa putative endochitinase; TI, trypsin inhibitor. The molecular weights of the markers are noted on the right;

FIG. 14 shows SDS-PAGE gel analysis of the reaction products after a Q Sepharose Fast Flow purified aspartic endoproteinase preparation was incubated in acid conditions for 1 minute and 7 hours. AP denotes the 30.5 kDa polypeptide; 27.9 denotes the 27.9 kDa putative endochitinase; TI, trypsin inhibitor. M, molecular weight markers (Precision, Biorad);

FIG. 15 shows denaturing size exclusion chromatography of the reaction products after a Q Sepharose Fast Flow purified aspartic endoproteinase was incubated in acid conditions for 1 minute and 7 hours respectively. The molecular weight size markers are: 1, ribonuclease A 13.7 kDa; 2, aprotinin 6.5 kDa; 3, substance P 1,347 Da; 4, N-benzoyl-gly-phe (hippuryl-phe) 326 Da; 5, phe 165 Da;

DETAILED DESCRIPTION OF THE PREFERRED EMBODIMENTS

During the studies leading to the present invention two aspartic endoproteinases have been found which seem to participate in the enzymatic degradation of vicillin-class globulins in cocoa beans under the conditions of fermentation.

Aspartic endoproteinases as such are a widely distributed class of proteases in animals, microbes, viruses and plants. All aspartic endoproteinases contain two aspartic residues at the active site and are active at acidic pH. In most of the aspartic endoproteinases, the catalytic aspartic residues are contained in a common Asp-Thr-Gly motif present in both lobes of the enzyme, with plant aspartic endoproteinases containing Asp-Ser-Gly at one of the sites.

Many aspartic proteinases have been detected or purified in monocots and dicots, which are either heterodimeric or monomeric. The sequences of corresponding genes predict that the active heterodimeric enzymes are derived from the processing of a single proprotein.

Though the genes and predicted proproteins for both monomeric and dimeric plant aspartic endoproteinases are quite similar they differ from mammalian and microbial counterparts by the presence of a 100 amino acids insert (a so called plant specific insert: PSI) which is absent in mammalian and microbial aspartic proteinases. This insert divides the protein in two regions: an amino-terminal and a carboxy-terminal region which show a relatively high similarity to each other and to mammalian and microbial enzymes. The amino-terminal region contains the two active sites Asp-Thr-Gly (DTG) and Asp-Ser-Gly (DSG) (FIG. 2). Although the positions of six cysteine residues are conserved, the PSI from different species are less homologous with each other than are the amino- and carboxy-terminal regions.

In view of this knowledge the conserved region has been utilized to obtain the nucleotide and amino acid sequence of aspartic endoproteinase (TcAP1, SEQ ID No. 1) from cacao bean (clone ICS 95) as follows:

A 1 kb internal fragment of the aspartic proteinase from cacao bean was amplified by RT-PCR using degenerate oligonucleotides that had been chosen according to an alignment of known aspartic endoproteinase sequences and a selection of conserved regions. Based on the sequence of this fragment, primers were designed to amplify 5'- and 3'-end. Afterwards, a full-length cDNA (TcAP1b, SEQ ID No. 6) was obtained by ligation of the 3' and 5' fragment using the BamH I restriction site and another one (TcAP1a, SEQ ID No. 4) was amplified using primers specific to both extremities (FIG. 3).

TcAP1a (SEQ ID No. 4) and TcAP1b (SEQ ID No. 6) nucleotide sequences differ only by 6 base pairs. Some of these differences are also found in the partial 1 kb fragment. Three of the differences lead to amino acid changes in the encoded protein (Table 1). The molecular weight and the pI of the protein are not changed.

TABLE 1

Differences observed in the nucleotide sequences from the different cDNA fragments obtained by PCR and their impact on the protein sequence.

| Position | 1 kb fragment | TcAP1a (SEQ ID No. 4) | TcAP1b (SEQ ID No. 6) | Altered residue |
| --- | --- | --- | --- | --- |
| 318 |  | T | A | L-----M |
| 431 | C | C | T | No change |
| 636 | G | G | A | A-----T |
| 764 | T | C | T | No change |
| 1189 | C | T | C | V-----A |
| 1376 | C | C | T | No change |

These differences may be explained by mistakes performed by polymerase enzymes during the PCR reactions. Another explanation could be that TcAP1a and TcAP1b are two different alleles from the same gene that we will name TcAP1. Furthermore, the 5'- and 3'-untranslated regions from TcAP1a and TcAP1b are identical. This argues rather for the presence of two alleles than for two different genes.

The cDNA sequences from TcAP1a isolated from cacao bean (clone ICS95) is 1784 bp long. A putative initiation start codon was assigned by comparison with other plant aspartic proteinase sequences. It is located 63 bp from the 5' end. The open reading frame is broken by a stop codon (TAA) at position 1605, followed by a putative polyadenylation signal (TATAAA) at position 1625.

TcAP1a encodes a 514 amino acid protein with a predicted molecular weight of 56 kDa and a pI of 5.05. The protein shows a high similarity with plant aspartic endoproteinases. Considering entire sequences, percent identity ranged between 59% observed with rice aspartic endoproteinase (Oryzasin A) and 87% with partial cotton sequence. A hydrophobicity analysis (FIG. 6A) reveals that TcAP1a encodes a hydrophilic protein with a very hydrophobic N-terminal end, indicating the presence of a signal peptide. Two catalytic triads (DTG and DSG) are also present.

The nucleotide and amino acid sequence of aspartic endoproteinase (TcAP2), from cacao bean (clone CCN51) was obtained as follows:

A 1 kb internal fragment of the aspartic endoproteinase from cacao bean was amplified by RT-PCR using degenerate oligonucleotides selected as above. Based on the sequence of this fragment, primers were designed to amplify 5'- and 3'-end. Afterwards, a full-length cDNA (TcAP2, SEQ ID No. 5) was amplified using primers specific to both extremities (FIG. 4).

The cDNA sequence from TcAP2 isolated from cacao bean (clone CCN51) is 1828 bp long. An initiation start codon is located 62 bp from the 5' end. The open reading frame is broken by a stop codon (TAA) at position 1606, followed by a putative polyadenylation signal (TATAAA) at position 1669.

TcAP2 encodes a 514 amino acid protein with a predicted molecular weight of 56 kDa and a pI of 5.31. The protein shows a high similarity with plant aspartic endoproteinases. Considering entire sequences, percent identity ranged between 57% observed with rice aspartic endoproteinase (Oryzasin A) and 77% with partial cotton sequence. A hydrophobicity analysis (FIG. 6B) reveals that TcAP2 encodes a hydrophilic protein with a very hydrophobic N-terminal end, indicating the presence of a signal peptide. Two catalytic triads (DTG and DSG) are also present.

A comparison of TcAP1a (SEQ ID NO:1), TcAP1b (SEQ ID NO:3) and TcAP2 (SEQ ID NO:2) is shown in FIG. 5. Each of the sequences shown in FIG. 5 has endoproteinase activity. One skilled in the art would appreciate from FIG. 5, that substitutions and/or deletions can be made while conserving the endoproteinase acitivity of the polypeptide. The comparison of SEQ ID NO:1 and SEQ ID NO:2 as shown in FIG. 5 based on the standard methods of alignment, reveals that at least 139 amino acid residues can be substituted while maintaining endoproteinase activity. When making variants of the above sequences, it is preferable that no more than 139 amino acid residues and more preferable that no more than 110 of the amino acid residues are substituted or deleted. One skilled in the art will also appreciate from the examples below how to determine whether the variant produced has aspartic endoproteinase activity.

EXAMPLES

The following examples illustrate the invention without limiting it to the same.

Cacao (*Theobroma cacao* L.) beans from ripe pods of clones ICS 95, CCN51 and EET95 were provided by Nestlé ex-R&D Center Quito (Ecuador). The beans were taken from the pods immediately after arrival at the laboratory (4–5 days after harvesting). The pulp and the seed coat were eliminated and the cotyledons were frozen in liquid nitrogen and stored at −80° C. until use.

Example 1

Preparation of mRNA

Two beans were grounded in liquid nitrogen to a fine powder and extraction was directly performed with a lysis buffer containing 100 mM Tris HCl pH8, 1% SDS and 0.1M β-mercaptoethanol. RNA was extracted with one volume phenol/chloroform/isoamylalcohol (25/24/1) and centrifuged at 8000 rpm for 10 min at 4° C. The aqueous phase was washed three times with chloroform/isoamylalcohol (24/1). RNA was precipitated with 0.3M sodium acetate pH 5.2 in two volumes of ethanol. The RNA pellet obtained after centrifugation was resuspended in 100 mM Tris HCl pH 8 and a second precipitation with 2M lithium chloride was performed. The RNA pellet was washed with 70% ethanol and resuspended in DEPC treated water.

Example 2

Cloning of Aspartic Proteinase cDNAs

A search for aspartic proteinase sequences in the GenBank database led to the identification of several plant sequences. A multiple alignment of these sequences revealed the presence of conserved regions, which have been used to design two degenerate oligonucleotides:

A sense primer, pAP0 (SEQ ID No. 7) (5'-GAYACNGGNAGYTCYAAYYTVTGG) has been synthesised according to the sequence Asp-Thr-Gly-Ser-Ser-Asn-Leu-Trp (SEQ ID No. 17), which contains an active site (Asp-Thr-Gly) of the protein.

An antisense primer pAP4r (5'-CCATMAANACRTCNCCMARRATCC) (SEQ ID No. 8) has been synthesised according to the sequence Trp-Ile-Leu-Gly-Asp-Val-Phe (SEQ ID No. 18), located in the C-terminal part of the protein.

Total RNA as prepared in example 1 was used to synthesize first strand cDNA with the SMART PCR cDNA Synthesis Kit (Clontech, USA). Synthesis has been performed exactly as described in the kit instructions using 1 µg of total RNA and the Superscript™ II MMLV reverse transcriptase (Gibco BRL, USA). After synthesis, cDNA was used directly for PCR or kept at −20° C.

Specific cDNA amplification was performed with 2 µl first strand cDNA in 50 µl buffer containing 10 mM Tris-HCl pH 8.8, 50 mM KCl, 1.5 mM MgCl₂, 0.001% (w/v) gelatin, 0.25 mM dNTP's, 30 pmoles of pAP0 and pAP4r primers and 5 units of Taq DNA polymerase (Stratagene, USA). Amplification was performed in a Bio-med thermocycler 60 (B. Braun). A first denaturation step (94° C., 2 min) was followed by 30 cycles of denaturation (94° C., 1 min), primer annealing (40° C., 1.5 min) and extension (72° C., 2 min). The extension time was increased by 3 sec at each cycle. Amplification was ended by a final extension step (72° C., 10 min). The amplified fragment was cloned in pGEM®-T Easy vector and sequenced.

TcAP1 and TcAP2 full-length cDNAs were cloned using Rapid Amplification cDNA Ends PCR (RACE PCR). For TcAP1, the Marathon™ cDNA Amplification Kit (Clontech, USA) was used. Poly A+RNA purified from total RNA (150 µg) with the Oligotex mRNA kit (QIAGEN, Germany) were used for the synthesis of double strand cDNA and a Marathon cDNA adaptor was ligated at both ends of the cDNA. These two steps have been performed according to the instructions of the Marathon™ cDNA Amplification Kit. For TcAP2, single strand cDNA has been synthesised from total RNA according to the SMART™ RACE cDNA Amplification Kit (Clontech, USA).

RACE PCR was performed with 5 µl Marathon adaptor-ligated double strand cDNA or 2.5 µl SMART single strand cDNA in 50 µl buffer containing 40 mM Tricine-KOH pH 9.2, 15 mM KOAc, 3.5 mM Mg(OAc)₂, 3.75 µg/ml BSA, 0.005% Tween-20, 0.005% Nonidet-P40, 0.2 mM dNTP's, 0.2 µM of each primer and 1 µl Advantage 2 Polymerase mix (Clontech, USA). Amplification was performed via touch-down PCR, in a Bio-med thermocycler 60 (B. Braun).

A first denaturation step (94° C., 1 min) was followed by:

5 cycles including denaturation at 94° C. for 30 sec and annealing/extension at 72° C. for 7 min;

5 cycles including denaturation at 94° C. for 30 sec and annealing/extension at 70° C. for 7 min; and 25 cycles including denaturation at 94° C. for 20 sec and annealing/extension at 68° C. for 7 min.

For TcAP1, two specific primers were paired with the AP1 primer, specific to the Marathon cDNA Adaptor provided in the Marathon kit:

ICS5 for 5'RACE PCR reaction (5'GCAGCCACCAGCACAAAGTCCAG) (SEQ ID No. 9)

ICS3 3'RACE PCR reaction (5'CGGTTGGAAATGCTGTGCCTGTGTGG) (SEQ ID No. 10)

For TcAP2, two specific primers were paired with the UPM (Universal Primer Mix) primer that recognises the SMART sequence:

CCN5 for the 5'RACE PCR reaction (5'ATGTGTGCTTGCCCTTGTAGTGG) (SEQ ID No. 11)

CCN3 for the 3'RACE PCR reaction (5'CCGCAATGTAGATGAAGAAGCAGGTGG) (SEQ ID No. 12)

The amplified fragments were cloned in pGEM®-T Easy vector and sequenced. The sequence information obtained after the sequencing of RACE fragments was used to design new oligonucleotides in order to amplify the full length fragments:

TcAP1

TcAP1, sense primer (5'TCTGCTCAGCTTTTCTTGTCG) (SEQ ID No. 13)

TcAP1r, reverse primer (5'GGATCACATGAAATTCTTAAACAAAGTGC) (SEQ ID No. 14).

TcAP2

TcAP2, sense primer (5'CTAATACGACTCACTATAGG) (SEQ ID No. 15)

TcAP2r, reverse primer (5'ATCTGTGACTGTTGATAAAAAGC) (SEQ ID No. 16)

PCR reaction was performed exactly as for the amplification of 5'- and 3'-RACE fragments with one denaturation step (95° C., 1 min) followed by 35 cycles of denaturation (94° C., 30 sec), primer annealing (63° C., 1 min) and extension (72° C., 2 min). The extension time was increased by 3 sec at each cycle. Amplification was ended by a final extension step (72° C., 10 min). The amplified fragment TcAP1 and TcAP2 were cloned in pGEM®-T Easy or pGEM®-T vectors respectively and sequenced.

Furthermore, a cloning strategy was also used to obtain the full-length TcAP1 cDNA. 5'- and 3'-RACE fragments overlap for 200 base pairs. In this overlapping region an unique restriction site BamH I is present. Both fragments have been isolated using BamH I and EcoR I (present in the plasmid) and subcloned directly in pBS+ (Stratagene, USA) using the same restriction enzymes.

Example 3

Sequencing and Analysis of DNA Sequences cDNA sequencing has been performed according to standard techniques (Maniatis, A Laboratory Manual, Cold Spring Harbor, 1992). Sequence analysis and comparison were done using DNAStar programme. The sequences are shown under SEQ ID Nos. 1 and 2.

Example 4

Expression of TcAP1a and TcAP2 in Cacao Plants

For the Northern blot total RNA was separated on 1.5% agarose gel containing 6% formaldehyde in 20 mM MOPS, 5 mM NaOAC, 1 mM EDTA pH 7. After electrophoresis, RNA was blotted onto nylon membranes (Appligene) and hybridized with $^{32}$P-labeled TcAP1a or TcAP2 probe at 65° C. in 250 mM Na-phosphate buffer pH 7.2, 6.6% SDS, 1 mM EDTA and 1% BSA. Membranes were washed three times at 65° C. for 30 min in 2×SSC, 0.1%SDS; in 1×SSC, 0.1% SDS and finally in 0.5×SSC, 0.1%SDS.

TcAP1a probe was amplified by PCR using TcAP1 and TcAP1r primers and TcAP2 probe with the following primers:

TcAP2b: a sense primer (5'-CTATAGGGCAAGCAGTGGTAACAAC) (SEQ ID No. 19)

TcAP2br: an antisense primer (5'-TGACCTAAAGGCAAATCCTAGTTTC) (SEQ ID No. 20).

PCR reaction was performed with 1 µl template cDNA in 50 µl buffer containing: 40 mM Tricine-KOH pH 8.7, 15 mM KOAc, 3.5 mM Mg(OAc)$_2$, 3.75 µg/ml BSA, 0.005% Tween-20, 0.005% Noninet-P40, 0.2 mM dNTP's, 0.2 µM of each primer and 1 µl 50×Advantage 2 polymerase Mix (Clontech, USA). Amplification was performed in a Biomed thermocycler 60 (B. Braun). A first denaturation step (94° C., 1 min) was followed by 30 cycles of denaturation (94° C., 30 sec), primer annealing (63° C., 1.5 min) and extension (72° C., 2 min). The extension time was increased by 3 sec at each cycle. Amplification was ended by a final extension step (72° C., 10 min).

Both fragments were purified with Strataprep PCR purification kit (Stratagene, USA) and labelled by the random priming procedure (rediprime™ II, Amersham Pharmacia Biotech).

Northern blot analysis with RNA purified from mature cacao beans produced by different trees, CCN51, EET95 and ICS95 reveals that TcAP1a and TcAP2 are both expressed in beans produced by the three different trees (FIG. 7A). However, TcAP2 is much more strongly expressed than TcAP1a indicating that it might be the major aspartic endoproteinase in cacao beans. RT-PCR experiments (FIG. 7B) are in agreement with these results. Confirmation of the idea that TcAP2 is the major aspartic endoproteinase activity in the bean is provided by the N-terminal sequencing of a purified native protein, which has the same sequence than TcAP2. Finally, the RT-PCR results presented in FIG. 7B also clearly show that both genes are expressed in leaves.

Similar experiments performed with RNA purified from cacao beans at different stages of maturation (FIG. 8) confirm that TcAP1 is less expressed than TcAP2 in developing and mature beans. TcAP1 and TcAP2 expression increase slightly during maturation and decrease in mature beans. TcAP2 is mainly expressed in early bean developmental stages suggesting that the synthesis of new aspartic endoproteinase falls as the bean matures.

During germination, the expression of TcAP2 is relatively stable in contrary to that of TcAP1, which increases after a few days of germination with a maximum at days 4 and 7. A strong expression is also detected at 49 days after imbibition (FIG. 9).

Example 5 cDNA Expression in Yeast Heterologous System

The coding sequences of TcAP1a and TcAP2 were overexpressed in the yeast heterologous system Yarrowia lipolytica.

TcAP1a and TcAP2 were overexpressed under the control of a synthetic XPR2-derived promoter hp4d present on the Yarrowia lipolytica expression/secretion plasmid pNFF296. For both cDNA, in order to excrete the recombinant protein in the culture medium the signal sequence (first 24 amino acids, predicted as according to Nielsen et al., Protein Engineering 10 (1997), 1–6 was replaced by a lipase signal sequence present on the Yarrowia lipolytica expression/secretion plasmid pNFF296.

TcAP1a cloned in pGEM-T Easy was used as template for the amplification of the cDNA sequence coding for a mature protein without a putative signal sequence.

Two primers were used for the amplification of TcAP1a:
Primer C089
(5'-CCGGCCTCTTCGGCCGCCAAGCGAATATCCAAT GAGAGATTGGTCAG) (SEQ ID No. 21)
primes at the 5' end of the predicted mature TcAP1a cDNA and introduces a SfiI site allowing cloning in frame to a hybrid XPR2-lipase signal sequence present on the Yarrowia lipolytica expression/secretion plasmid pNFF296.
Primer C090
(5'-CCGGCCCACGTGGCCTTAGTGGTGGTGTGCAG CCTCGGCAAATCCAAC) (SEQ ID No. 22)
primes at the 3' end of the mature TcAP1a cDNA and introduces in-frame a 3×HIS sequence just before the stop codon and the SfiI cloning site in front of the lipase terminator of pNFF296.

TcAP2 cDNA cloned in pGEM-T was used as template for the amplification of the sequence coding for the mature protein without a putative signal sequence. Two primers were used for the amplification of TcAP2:
Primer C091
(5'-CCGGCCTCTTCGGCCGCCAAGCGAGTATCCA ATGATGGGCTGGTTAG) (SEQ ID No. 23)
primes at the 5' end of the predicted mature TcAP2 cDNA and introduces a SfiI site allowing cloning in frame to a hybrid XPR2-lipase signal sequence present on the *Yarrowia lipolytica* expression/secretion plasmid pNFF296.
Primer C092
(5'-CCGGCCCACGTGGCCTTAGTGGTGGTGTGCCGC CTCGGCGAAGCCGAC) (SEQ ID No. 24)
primes at the 3' end of the mature TcAP2 cDNA and introduces in-frame a 3xHIS sequence just before the stop codon and the SfiI cloning site in front of the lipase terminator of pNFF296.

Amplification was performed with 1 μl of template cDNA (20 ng) in 10 mM KCl, 6 mM $(NH_4)_2SO_4$, 20 mM Tris-HCl, pH 8.0, 0.1% Triton X-100, 2 mM $MgCl_2$, 0.2 mM of each dNTP, 10 μg ml$^{-1}$ BSA, 0.25 μM of each primers and 3 units of Pfu DNA polymerase (Stratagene, USA). PCR was performed in a Stratagene RoboCycler (Stratagene, USA). A first cycle (95° C.-5 min, 50° C.-1 min, 72° C.-3 min) was followed by 30 cycles (95° C.-1 min, 50° C.-1 min, 72° C.-3 min) and a final cycle (95° C.-1 min, 50° C. −1 min, 72° C.-10 min). The PCR products were purified using the Qiaquick PCR purification Kit (Qiagen INC., USA), digested with SfiI, and subsequently ligated into vector pNFF296 previously digested with SfiI. This ligation was used to transform *E. coli* BZ234 (Biozentrum, University of Basel, Switzerland). Constructs were selected on LB plates supplemented with 50 μg ml$^{-1}$ kanamycine, analyzed by mini plasmid-preparations plus restriction enzyme digestion and finally by DNA sequence analysis. The resulting plasmids containing TcAP1a or TcAP2 were called pCY329 and pCY330, respectively.

The *Yarrowia lipolytica* host strain YLP3 was derived from strain po1f (MatA ura3-302 leu2-270 xpr2-322 axp-2 SUC2) by transforming said strain to leucine prototrophy with a 5.1 kb SalI fragment carrying the *Yarrowia lipolytica* wild-type LEU2 gene (J.-M. Nicaud, pers. comm.) and selecting for LEU2 convertants. The *Yarrowia lipolytica* host strain was streaked on a YPD agar plate (1% Difco Bacto Yeast Extract, 2% Difco Bacto Peptone, 2% Glucose, 2% Difco Bacto Agar) and grown overnight at 28° C. 4 ml of liquid YPD pH 4.0 (1% Difco Bacto Yeast Extract, 1% Difco Bacto Peptone, 1% Glucose, 50 mM Citrate buffer at pH 4.0) were inoculated with freshly grown cells of the YPD plate and grown in a tube on a rotary shaker (200 rpm, 28° C., 8–9 hrs). Of this preculture an adequate amount was used to inoculate 20 ml YPD pH 4.0 in a 250 ml Erlenmeyer flask without baffles. This culture was shaken in a rotary shaker at 200 rpm at 28° C. (over night) until a cell titration of $10^8$ ml$^{-1}$ has been reached. The cells were centrifuged for 5 min at 3000 g, washed with 10 ml of sterile water and re-centrifuged. The cellular pellet was suspended in 40 ml 0.1 M lithium acetate pH 6.0 (adjusted with 10% acetic acid) and shaken in a 250 ml Erlenmeyer at 140 rpm at 28° C. for 60 minutes. The cells were again centrifuged for 5 min at 3000 g. The cellular pellet was suspended in 2 ml lithium acetate pH 6.0 and the competent cells were kept on ice until transformation.

One hundred microliters of competent cells were mixed with 5–20 μl plasmid linearized with NotI and 50 μg carrier DNA (herring sperm DNA sonicated to 100–600 bp, Promega, USA) in a 2 ml tube and incubated for 15 minutes at 28° C. 700 μl 40% PEG4000, 0.1 M lithium acetate pH 6.0 were added and the tubes heavily agitated at 240 rpm on a rotary shaker at 28° C. for 60 minutes. A volume of 1.2 ml of 0.1 M lithium acetate pH 6.0 was added and mixed. 250 μl were plated on selective agar plates (0.17% Difco Bacto Yeast Nitrogen Base w/o amino acid and ammonium sulfate, 1% glucose, 0.006% L-leucine, 0.1% sodium glutamate, 0.1% Difco Bacto Casamino Acids, 2% agar). The expression plasmid pNFF296 carries a defective URA3 allele allowing for the selection of multiple integration of the expression secretion cassette in the YLP3 host strain.

Transformants (Ura$^+$) were re-isolated on selective medium (0.17% Difco Bacto Yeast Nitrogen Base w/o amino acid and ammonium sulfate, 1% glucose, 0.006% L-leucine, 0.1% sodium glutamate, 0.1% Difco Bacto Casamino Acids, 2% agar). A series of clones was grown in shake-flasks to check for expression and secretion of aspartic proteinase into the culture medium.

Small patches of cells were streaked on YPD agar plates and grown overnight at 28° C. The thin layers of grown cells were used to inoculate 50 ml DMI medium in 500 ml Erlenmeyers with 4 lateral baffles. DMI medium contains per liter: $KH_2PO_4$, 10 g; $MgSO_4,7H_2O$, 2.5 g; glucose, 20 g; Trace elements solution, 5.1 ml; Vitamins solution, 17 ml; urea, 3 g. Urea was dissolved in 15 ml water and sterile filtered. The initial pH of the medium was adjusted to 5.0. The cultures were shaken at 140 rpm on a rotary shaker at 28° C. for three days. Aliquots of the cultures were centrifuged at maximum speed (3000 g) for 15 min. and the supernatant used for the determination of the aspartic endoproteinase activity.

Aspartic endoproteinase activity was assayed at 42° C. in a 900 μl reaction medium containing 0.2M sodium citrate buffer pH3.0, 10 mg/ml bovine haemoglobin and 150 μl yeast culture supernatant. To stop the reaction aliquots (80 μl) were added to an equal volume of TCA 8% and the precipitated protein removed by centrifugation at 13000 g. 20 μl supernatant were mixed to 250 μl O-phthaldialdehyde (OPA) reagent (50 mM sodium tetraborate, 1% SDS, 5.96 mM OPA (dissolved in 1 ml methanol) and 1.43 mM β-mercaptoethanol. Activity was then determined measuring OD at 340 nm and expressed in pmole leucine produced per mg protein. For this, we use the following linear equation ($OD_{340\ nm}$=0.0156 pmoles+0.0088), which was determined using a standard curve with L-leucine (0 to 80 pmoles). Protein concentration was determined by Bradford assay (Biorad).

A strong activity could be detected in 12 independent clones transformed with the pCY330 construct (TcAP2). Further characterization of the TcAP2 recombinant protein was done using one clone named pCY330-33. Comparison of activity measurement with supernatant from pCY330-33 and pNFF296 (control) clearly shows that no activity is detected in the control (1.44±0.52 pmoles L-leucine/min/mg protein) and that hydrolysis of bovine haemoglobin occurs in presence of supernatant from pCY330-33 (25.8±1.45 pmoles L-leucine/min/mg protein) (FIG. 10). This activity demonstrates clearly that active recombinant TcAP2 protein is produced by pCY330-33.

The recombinant TcAP2 endoproteinase detected in pCY330-33 hydrolyses bovine haemoglobin with an optimum at pH 3 (FIG. 11). Only slight activity could be detected for pH higher than 5.

The endoprotease activity detected in the medium of pCY330-33 (TcAP2) is completely inhibited by 2 μM pepstatin, a specific inhibitor for aspartic endoproteinase. The pepstatin insensitive activity (1.91±1.26 pmoles L-leucine/min/mg protein, 6.65%) is in the same range as that one measured for the control strain (2.26±1.26 pmoles L-leucine/min/mg protein, 7.8%). Other inhibitors such as 1.10 phenanthroline (metallo proteases), DCI (serine proteases) and E64 (cysteine proteases) have no effect on TcAP2 activity (FIG. 12).

The data presented here clearly show that the culture medium in which yeast pCY330-33 was grown contained a protein able to hydrolyse bovine haemoglobin. Maximum activity at acidic pH and inhibition by pepstatin are two specific biochemical features for aspartic proteinases.

Example 6

Native Protein Purification

Approximately 25 g of the frozen EET 95 cacao beans were ground to a fine powder using liquid nitrogen and extracted with cold acetone/water/5 mM sodium ascorbate (80/20/5) according to a modified procedure of Hansen et al., J. Sci. Food Agric. 77 (1998), 273–281, to remove the majority of the fat and phenolic compounds. This procedure resulted in approximately 11.3 g of a fine acetone powder.

Acetone powder (5 g) was extracted twice with 500 ml of buffer A (10 mM sodium phosphate pH 7.8, 2 mM EDTA, 10 mM sodium acetate) for 1 hour at 4° C. After centrifugation (7840 g, 25 min, 4° C.) the combined supernatants were made sequentially to 30% and 60% ammonium sulphate. All ammonium sulphate fractions were assayed for activity and the 60% ammonium sulphate precipitate was found to have the highest level of endoproteinase activity and was dialysed against buffer B (50 mM sodium phosphate pH 7.8, 1 mM EDTA).

Using an Akta Purifier (Pharmacia), 2×10 ml of dialysed 60% ammonium sulfate precipitate were loaded on a HiLoad 26/10 Q Sepharose Fast Flow column (Pharmacia) at 8–10° C. After loading, the column was washed with 5 column volumes of 20 mM Tris-HCl pH 8, then eluted with a linear gradient of 10 column volumes of the same buffer supplemented with 1 M NaCl. The flow rate of the column was 10 ml/min and 5 ml fractions were collected.

Fractions from the Q Sepharose Fast Flow column were assayed for aspartic endoproteinase activity and fractions showing the highest level of activity (#65–80) were pooled. The pooled fractions (75 ml) were concentrated to 2.2 ml using "Ultrafree Biomax" 4 ml filters (5 kDa Mw cut off), and loaded onto a Sephacryl S-200 HiPrep 16/60 size exclusion column (Pharmacia) equilibrated with 10 mM Tris-HCl pH 8 and 500 mM NaCl at a flow rate of 0.5 ml/min. 1 ml fractions were collected and assayed for aspartic endoproteinase activity. The most active fractions were concentrated into three pools (#53–56, #57–64, #65–68) using "Ultrafree Biomax" filter. Protein concentration was determined with the micro BCA protein assay kit (Pierce, Inc) using BSA as a standard.

The most active pool (#57–64) with a specific activity of 1054 units/mg protein (1 unit=100 ng leucine equivalent produced/min) has been subjected to SDS-PAGE. This gel (FIG. 13) shows that this fraction contains several polypeptides. N-terminal sequencing of the major bands revealed that only the 30.5 kDa band (DSEETDIVAL) (SEQ ID No. 25) corresponded exactly to the sequence of the cacao TcAP2 protein of the present invention. The other main polypeptides in the preparation were found to be putative protein body proteins. The 27.9 kDa polypeptide N-terminal sequence (TVISTYWGQNGFEGT) (SEQ ID No. 26) showed the strongest homology (76.9%) with a *Glycine max* acid chitinase III-A (accession AB007127). Thus, it is likely that the 27.9 kDa protein is an acid chitinase. The N-terminal sequence obtained for the 20.2 kDa polypeptide (ANSP) (SEQ ID No. 27) confirmed that this band is the cacao trypsin inhibitor protein (accession X56509). In order to verify whether the endoproteinase was effectively composed of two subunits (29 and 13 kDa) (Voigt et al., J. Plant Physiol. 145 (1995), 299–307), several polypeptides smaller than 15.6 kDa were also sequenced. All the examined bands were found to be fragments of the 20.2 kDa cacao trypsin inhibitor protein and none corresponded to a putative 13 kDa of TcAP2. Furthermore, the fact that the 30.5 kDa polypeptide contains both catalytic triads ($D^{108}TG$, $D^{295}SG$) supports the idea that this polypeptide alone is proteolytically active. Therefore, TcAP2 is a novel monomeric aspartic endoproteinase.

Example 7

Characterisation of the Native Purified Aspartic Endoproteinase Activity

Inhibitor Sensitivity

The inhibitor sensitivity of the native aspartic endoproteinase was determined in 300 μl reactions containing 200 mM sodium citrate, pH 3, 10 mg/ml bovine hemoglobin, and 5 μl of size exclusion purified pool #57–64 (2.4 μg protein/μl). The inhibitors were added to give a final concentration of 2 μM pepstatin, 2 mM 1,10 phenanthroline, 100 μM dichloroisocoumarin (DCI), 10 μM E-64. The enzyme activity was determined as described in example 5. The fact that only pepstatin A inhibits completely the activity (Table 2) confirms that the protease activity purified is an aspartic endoproteinase.

TABLE 2

Inhibitor sensitivity of the purified aspartic endoproteinase activity. Two replicates were done for each test.

| Inhibitor | mM | Remaining Activity % |
|---|---|---|
| — | — | 100% |
| Pepstatin A | 0.002 | 0% |
| 1,10 Phenanthroline | 2.0 | 86% |
| E-64 | 0.01 | 88% |
| DCI | 0.1 | 90% |

Determination of the optimum pH: the activity test performed at different pH values indicated that the purified enzyme had an optimal activity at pH 3.0 (data not shown).

Example 8

Analysis of the products formed when a partially purified aspartic endoproteinase preparation is incubated in acid conditions.

To examine the peptides produced by the native cacao seed aspartic endoproteinase, a Q Sepharose Fast Flow partially purified preparation of TcAP2 (197 μg protein, 1.35 units of activity/μl; specific activity 821 units/mg protein) was incubated in acid conditions. 120 μl of the partially purified enzyme were mixed with 30 μl 1 M sodium citrate pH 3. Samples of 4 μl and 70 μl were taken out just before incubation at 42° C. (t=1 min) and after seven hours. The 4 μl samples were put in SDS gel loading buffer for SDS-PAGE analysis. The reaction in the 70 μl samples was stopped by adding SDS to 1% final concentration, the samples were freeze-dried, solublized with 100 μl 6M urea, 20 mM sodium phosphate pH 7, loaded on a Superdex Peptide HR 10/30 column (Amersham Pharmacia Biotech) and eluted with 6M urea, 20 mM sodium phosphate pH 7 at ambient temperature.

The gel presented in FIG. 14 shows that after 7 hours, nearly all the proteins seen in the 1 min sample were substantially hydrolysed. Only two significant bands remain, one of which corresponds to a reduced amount of the 30.5 kDa cacao aspartic endoproteinase polypeptide indicating an enhanced resistance of the aspartic endoproteinase towards autocatalytic degradation. When the products of the aspartic endoproteinase digestion were examined by high resolution size exclusion chromatography (FIG. 15), a significant proportion of small oligopeptides were detected, with a large percentage of the peptides having sizes ranging between 2 and 70 amino acids. This observation indicates that reacting the main cacao seed aspartic endoproteinase (TcAP2) with proteins can generate a significant level of very small peptides, and thus that the action of this enzyme could generate a significant proportion of the cocoa flavor precursor peptides found in fermented cocoa beans.

What is claimed is:

1. A recombinant aspartic endoproteinase selected from the group consisting of SEQ ID NO:1; SEQ ID NO:2 and SEQ ID NO:3.

2. A purified aspartic endoproteinase polypeptide comprising an amino acid sequence selected from the group consisting of SEQ ID NO:1; SEQ ID NO:2; and SEQ ID NO:3.

3. An isolated nucleic acid molecule, comprising a DNA sequence encoding an aspartic endoproteinase polypeptide according to claim 1.

4. The DNA sequence according to claim 3, which is identified by SEQ ID NO:4; SEQ ID NO:5; or SEQ ID NO:6.

5. A vector comprising a DNA sequence according to claim 3.

6. A cell containing a recombinant DNA sequence according to claim 3.

7. The cell according to claim 6, wherein the cell is a plant cell.

8. The cell according to claim 7, wherein the plant cell is a cacao cell.

9. A transgenic plant, containing a cell according to claim 7.

10. A method for producing a cacao aspartic endoproteinase which comprises obtaining the DNA sequence according to claim 3 by recombinant techniques and utilizing the sequence to manufacture the cacao aspartic endoproteinase.

11. The method according to claim 10, wherein the aspartic endoproteinase is produced in a suitable cell.

12. The method according to claim 11, wherein the is a plant cell.

13. The method according to claim 12, wherein the plant cell is a cacao cell.

14. The method of claim 10, which further comprises utilizing the cacao aspartic endoproteinase to prepare a cocoa flavor.

15. The method of claim 14, wherein the cocoa flavor is prepared by subjecting a material suitable to yield cocoa flavor precursors to an enzymatic degradation by the aspertic endoproteinase.

* * * * *

UNITED STATES PATENT AND TRADEMARK OFFICE
CERTIFICATE OF CORRECTION

PATENT NO. : 6,790,650 B2
DATED : September 14, 2004
INVENTOR(S) : Bucheli et al.

It is certified that error appears in the above-identified patent and that said Letters Patent is hereby corrected as shown below:

Title page,
Item [56], References Cited, OTHER PUBLICATIONS, "J. Voight et al." reference, after "Developmental stage-dependent variation of" insert -- the levels of --.
"Hiraiwa Nagako et al." reference, change "Hiraiwa Nagako et al." to
-- Hiraiwa et al. --; and change "endopepetidase" to -- endopeptidase --.

Column 38,
Line 25, after "The method according to claim 11, wherein the" insert -- cell --.

Signed and Sealed this

Fourteenth Day of December, 2004

JON W. DUDAS
*Director of the United States Patent and Trademark Office*